(12) United States Patent
Nagashima et al.

(10) Patent No.: US 9,782,762 B2
(45) Date of Patent: Oct. 10, 2017

(54) SUBSTITUTED MONONUCLEAR RUTHENIUM COMPLEXES FOR CATALYSIS OF SYNTHETIC ORGANIC REACTIONS

(71) Applicants: KYUSHU UNIVERSITY, NATIONAL UNIVERSITY CORPORATION, Fukuoka-shi, Fukuoka (JP); SHIN-ETSU CHEMICAL CO., LTD., Tokyo (JP)

(72) Inventors: Hideo Nagashima, Kasuga (JP); Yusuke Sunada, Kasuga (JP); Hironori Tsutsumi, Kasuga (JP); Toru Hashimoto, Kasuga (JP); Koji Sakuta, Annaka (JP)

(73) Assignees: KYUSHU UNIVERSITY, NATIONAL UNIVERSITY CORPORATION, Fukuoka-Shi (JP); SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/771,765

(22) PCT Filed: Feb. 26, 2014

(86) PCT No.: PCT/JP2014/054715
§ 371 (c)(1),
(2) Date: Aug. 31, 2015

(87) PCT Pub. No.: WO2014/133014
PCT Pub. Date: Sep. 4, 2014

(65) Prior Publication Data
US 2016/0023197 A1 Jan. 28, 2016

(30) Foreign Application Priority Data
Mar. 1, 2013 (JP) ................................. 2013-040906

(51) Int. Cl.
*C22C 5/04* (2006.01)
*B01J 31/16* (2006.01)
(Continued)

(52) U.S. Cl.
CPC ........... *B01J 31/1608* (2013.01); *B01J 31/22* (2013.01); *C07C 5/03* (2013.01); *C07C 9/16* (2013.01); *C07C 13/10* (2013.01); *C07C 13/18* (2013.01); *C07C 15/073* (2013.01); *C07C 15/18* (2013.01); *C07C 29/14* (2013.01); *C07C 209/50* (2013.01); *C07C 213/00* (2013.01); *C07D 223/04* (2013.01); *C07F 7/08* (2013.01); *C07F 15/0046* (2013.01); *B01J 2231/323* (2013.01); *B01J 2231/643* (2013.01); *B01J 2231/645* (2013.01); *B01J 2531/821* (2013.01); *C07C 2531/16* (2013.01); *C07C 2531/22* (2013.01);
(Continued)

(58) Field of Classification Search
CPC ......................................................... C22C 5/04
USPC ........................................................ 420/462
See application file for complete search history.

(56) References Cited

U.S. PATENT DOCUMENTS 4,309,558 A   1/1982   Koga et al.
5,248,802 A   9/1993   Bank
(Continued)

FOREIGN PATENT DOCUMENTS

DE   28 10 032 A1   9/1978
EP   0 403 706 A2   12/1990
(Continued)

OTHER PUBLICATIONS

Jordan, V. C. Nature Reviews: Drug Discovery, 2, 2003, 205.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Brown, "Reductions by Lithium Aluminum Hydride", Organic Reactions, Chapter 10, pp. 469-493.
International Search Report issued in PCT/JP2014/054715 dated Apr. 28, 2014.
Komuro et al., "Thermal reaction of ruthenium bis(silyl) complex having a lutidine-based Si,N,Si ligand: formation of a μ-silyl(μ-silylene) diruthenium complex involving a 3c-2e Ru—Si—C interaction", Chem. Comm., 46, pp. 1136-1137, 2010.
(Continued)

*Primary Examiner* — Douglas M Willis
(74) *Attorney, Agent, or Firm* — Birch, Stewart, Kolasch & Birch, LLP

(57) ABSTRACT

Provided is a mononuclear ruthenium complex that comprises a ruthenium-silicon bond that is represented by formula (1) and that exhibits excellent catalyst activity in each of a hydrosilylation reaction, a hydrogenation reaction, and reduction of a carbonyl compound.

(1)

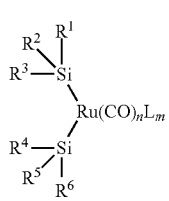

In formula (1), $R^1$-$R^6$ either independently represent an alkyl group, an aryl group, an aralkyl group or the like that may be substituted with a hydrogen atom or X, or represent a crosslinking substituent in which at least one pair comprising one of $R^1$-$R^3$ and one of $R^4$-$R^6$ is combined. X represents a halogen atom, an organoxy group, or the like. L represents a two-electron ligand other than CO and phosphine. When a plurality of L are present, the plurality of L may be the same as or different from each other. When two L are present, the two L may be bonded to each other. n and m independently represent an integer of 1 to 3 with the stipulation that n+m equals 3 or 4.

11 Claims, 2 Drawing Sheets

(51) Int. Cl.
| | | |
|---|---|---|
| *B01J 31/22* | (2006.01) | |
| *C07C 209/50* | (2006.01) | |
| *C07C 5/03* | (2006.01) | |
| *C07C 9/16* | (2006.01) | |
| *C07C 13/10* | (2006.01) | |
| *C07C 13/18* | (2006.01) | |
| *C07F 7/08* | (2006.01) | |
| *C07C 15/073* | (2006.01) | |
| *C07C 15/18* | (2006.01) | |
| *C07F 15/00* | (2006.01) | |
| *C07C 29/14* | (2006.01) | |
| *C07C 213/00* | (2006.01) | |
| *C07D 223/04* | (2006.01) | |

(52) U.S. Cl.
CPC ...... *C07C 2531/28* (2013.01); *C07C 2601/08* (2017.05); *C07C 2601/14* (2017.05)

(56) References Cited

U.S. PATENT DOCUMENTS

| | | |
|---|---|---|
| 5,559,264 A | 9/1996 | Bowman et al. |
| 8,124,711 B2 | 2/2012 | Hofmann et al. |
| 2004/0092759 A1 | 5/2004 | Westmeyer et al. |
| 2009/0171056 A1 | 7/2009 | Hofmann et al. |

FOREIGN PATENT DOCUMENTS

| | | |
|---|---|---|
| JP | 2009-533374 A | 9/2009 |
| JP | 2011-045798 A | 3/2011 |
| JP | 5032561 B2 | 9/2012 |
| WO | WO 96/05207 A1 | 2/1996 |
| WO | WO 2009/055912 A1 | 5/2009 |

OTHER PUBLICATIONS

Matsubara et al., "A Triruthenium Carbonyl Cluster Bearing a Bridging Acenaphthylene Ligand: An Efficient Catalyst for Reduction of Esters, Carboxylic Acids, and Amides by Trialkylsilanes", J. Org. Chem. 67, pp. 4985-4988, 2002.

Miyamoto et al., "Selective Reduction of Carboxylic Acids to Aldehydes by a Ruthenium-catalyzed Reaction with 1,2-BIS(dimethylsilyl)benzene", Chem. Lett. 41, pp. 229-231, 2012.

Motoyama et al., "Self-Encapsulation of Homogeneous Catalyst Species into Polymer Gel Leading to a Facile and Efficient Separation System of Amine Products in the Ru-Catalyzed Reduction of Carboxamides with Polymethylhydrosiloxane (PMHS)", J. Am. Chem. Soc. 127, pp. 13150-13151, 2005.

Okazaki et al., "[Ru(xantsil)(CO)($\eta$6-toluene)]: Synthon for a Highly Unsaturated Ruthenium(II) Complex through Facile Dissociation of the Toluene Ligand [xantsil = (9,9-dimethylxanthene-4,5-diyl)bis(dimethylsilyl)]", Organometallics, 27, pp. 918-926, 2008.

Okazaki et al., Synthesis, structure, and reactivity of hydridobis-(silylene)ruthenium(IV)-xantsil complexes (xantsil = (9,9-dimethylxanthene-4,5-diyl)bis(dimethylsilyl))—A stabilized form of key intermediates in the catalytic oligomerization-deoligomerization of hydrosilanes1, Can. J. Chem. 81: pp. 1350-1358 (2003).

Sasakuma et al., "Functional group-selective poisoning of molecular catalysts: a ruthenium cluster-catalysed highly amide-selective silane reduction that does not affect ketones or esters", Chem. commun., pp. 4916-4918, 2007.

Süss-Fink et al., "The Cluster Anion [HRu3(CO)11]—As Catalyst in Hydro-Formylatioin, Hydrogenation, Silacarbonylation and Hydrosilylation Reactions of Ethylene and Propylene", Journal of Molecular Catalysis, 16, pp. 231-242, (1982).

Takanashi et al., "Tetrasilacyclobutadiene and Cyclobutadiene Tricarbonylruthenium Complexes: [$\eta$4-(Bu2MeSi)4Si4]Ru(CO)3 and [$\eta$-(Me3Si)4C4]Ru(CO)3", Organometallics, 28, pp. 1248-1251, 2009.

Written Opinion of the International Searching Authorirty issued in PCT/JP2014/054715 dated Apr. 28, 2014.

Extended European Search Report issued Jul. 18, 2016, in European Patent Application No. 14756744.0.

Sunada et al., "Disilametallacycles as Platform for Stabilizing M(II) and M(IV) (M = Fe, Ru) Centers: Synthesis and Characterization of Half-Sandwich Complexes and their Application to Catalytic Double Silylation of Alkenes and Alkynes," Organometallics (2013), vol. 32, pp. 2112-2120.

\* cited by examiner

SUBSTITUTED MONONUCLEAR RUTHENIUM COMPLEXES FOR CATALYSIS OF SYNTHETIC ORGANIC REACTIONS

TECHNICAL FIELD

This invention relates to a mononuclear ruthenium complex having ruthenium-silicon bonds, and more particularly, to a mononuclear ruthenium complex having catalytic activity to three reactions: hydrosilylation reaction, hydrogenation reaction, and reductive reaction of carbonyl compounds.

BACKGROUND ART

Hydrosilylation reaction involving addition reaction of a Si—H functionality compound to a compound having a carbon-carbon double or triple bond is a useful means for synthesizing organosilicon compounds and is also industrially important synthetic reaction.

Pt, Pd and Rh compounds are known as catalysts for the hydrosilylation reaction. Most often used among them are Pt compounds as typified by Speier catalysts and Karstedt catalysts.

One of problems associated with Pt compound-catalyzed reactions is that the addition of a Si—H functionality compound to terminal olefin entails side reaction or internal rearrangement of olefin. Since this system does not display addition reactivity to internal olefin, unreacted olefin is left in the addition product. To complete the reaction, the olefin must be used previously in excess by taking into account the portion that is left behind due to side reaction.

Another problem is low selectivity between α- and β-adducts depending on the identity of olefin.

The most serious problem is that all Pt, Pd and Rh as the center metal are very expensive noble metal elements. Since metal compound catalysts which can be used at lower cost are desired, a number of research works have been made thereon. Among noble metals, Ru is available at relatively low cost. It would be desirable if Ru has a function to replace Pt, Pd, and Rh.

Patent Document 1 reports a Ru compound having a $\eta^6$-arene group and organopolysiloxanes bonded or vinylsiloxanes coordinated to Ru as the center metal. It is shown that this compound is useful in addition reaction of methylhydrogenpolysiloxane and methylvinylpolysiloxane. Since the reaction at 120° C. leads to low yields, the reaction must be carried out at a high temperature of 160° C. to achieve high yields.

Many patent documents relating to Ru catalysts are cited in Patent Document 1 as reference (Patent Documents 2 to 6). From the aspects of reactivity, selectivity, and cost, it cannot be said that any Ru catalysts are superior to noble metal element based catalysts.

As for hydrogenation reaction of olefins, Non-Patent Document 1, for example, reports reaction using a trinuclear ruthenium catalyst, but further improvements are desired from the aspects of reaction temperature and yields.

One known method for reducing carbonyl compounds is by using hydrogen in the presence of aluminum hydride, boron hydride or noble metal catalysts. For ketones and aldehydes among carbonyl compounds, there are known hydride promoters and hydrogenation noble metal catalysts which allow progress of reaction under mild conditions and are stable and easy to handle. For reducing carboxylic acid derivatives such as esters and amides, the main method uses strong reducing agents such as lithium aluminum hydride and borane (Non-Patent Document 2). However, since these reducing agents are flammable, water-prohibitive substances, they are awkward to handle. Also careful operation is necessary when the aluminum or boron compound is removed from the desired compound at the end of reaction. In addition, high-temperature/high-pressure hydrogen is necessary for the reduction of carboxylic acid derivatives.

There are reported many methods using methylhydrogenpolysiloxane or hydrosilane compound which is stable in air and easy to handle, as the reducing agent. For this reaction, addition of strong acids or Lewis acids is necessary as well as expensive noble metal catalysts. One recent report relates to reductive reaction of carbonyl compounds in the presence of relatively low cost ruthenium catalysts. In some examples, the catalyst is applied to reductive reaction of amides which requires rigorous conditions in the prior art. While illustrative examples of the ruthenium catalyst are given in Non-Patent Documents 3 to 6, there is a desire to have high activity catalysts displaying a greater turnover count.

CITATION LIST

Patent Documents

Patent Document 1: JP 5032561
Patent Document 2: US 20040092759
Patent Document 3: U.S. Pat. No. 5,559,264
Patent Document 4: EP 0403706
Patent Document 5: U.S. Pat. No. 5,248,802
Patent Document 6: DE 2810032

Non-Patent Documents

Non-Patent Document 1: G. Suss-Fink, et al., J. Mol. Cat. 1982, 16, 231
Non-Patent Document 2: W. R. Brown, Organic Reactions, 1941, 6, 470
Non-Patent Document 3: K. Miyamoto, et al., Chem. Lett. 2012, 229
Non-Patent Document 4: K. Matsubara, et al., J. Org. Chem. 2002, 67, 4985
Non-Patent Document 5: Y. Motoyama, et al., J. Am. Chem. Soc. 2005, 127, 13150
Non-Patent Document 6: H. Sasakuma, et al., Chem. Commun. 2007, 4916

SUMMARY OF INVENTION

Technical Problem

An object of the invention, which has been made under the above circumstances, is to provide a mononuclear ruthenium complex having ruthenium-silicon bonds that displays high catalytic activity to three reactions: hydrosilylation reaction, hydrogenation reaction, and reductive reaction of carbonyl compounds, and methods for carrying out hydrosilylation reaction, hydrogenation reaction, and reductive reaction of carbonyl compounds under mild conditions in the presence of the complex.

Solution to Problem

Making extensive investigations to solve the outstanding problems, the inventors have found that a specific mononuclear ruthenium complex having ruthenium-silicon bonds displays high catalytic activity to three reactions: hydrosilylation reaction, hydrogenation reaction, and reductive reaction of carbonyl compounds, and allows hydrosilylation reaction, hydrogenation reaction, and reductive reaction of carbonyl compounds to run under mild conditions. The invention is completed based on this finding.

Namely, the present invention provides the following.

[1] A mononuclear ruthenium complex having formula (1):

[Chemical Formula 1]

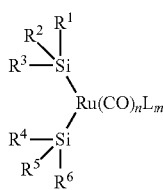

(1)

wherein $R^1$ to $R^6$ are each independently hydrogen, or an alkyl, aryl, aralkyl, organoxy, monoorganoamino, diorganoamino, monoorganophosphino, diorganophosphino, monoorganosilyl, diorganosilyl, triorganosilyl or organothio group which may be substituted with X, or at least one pair of any one of $R^1$ to $R^3$ and any one of $R^4$ to $R^6$, taken together, represent a crosslinking substituent; X is a halogen atom, organoxy, monoorganoamino, diorganoamino or organothio group; L is a two-electron ligand other than CO and phosphine, with the proviso that when a plurality of L's are present, they may be the same or different, and when two L's are present, they may bond together; n and m are each independently an integer of 1 to 3, and n+m is 3 or 4.

[2] The mononuclear ruthenium complex of [1] wherein L is at least one two-electron ligand selected from the group consisting of molecular hydrogen, amine, imine, nitrogen-containing heterocycle, arsine, alcohol, thiol, ether, sulfide, nitrile, isonitrile, aldehyde, ketone, $C_2$-$C_{30}$ alkene, $C_2$-$C_{30}$ alkyne, and triorganohydrosilane.

[3] The mononuclear ruthenium complex of [1] or [2] wherein n and m each are 2, and L is at least one ligand selected from sulfide, thiol, and triorganohydrosilane, with the proviso that two L's may bond together.

[4] The mononuclear ruthenium complex of [3] wherein $R^1$ to $R^6$ are each independently an alkyl, aryl or aralkyl group which may be substituted with X which is as defined above, L's are triorganohydrosilanes represented by H—$SiR^7R^8R^9$ and H—$SiR^{10}R^{11}R^{12}$ wherein $R^7$ to $R^{12}$ are each independently an alkyl, aryl or aralkyl group which may be substituted with X which is as defined above, at least one pair of any one of $R^1$ to $R^3$ and any one of $R^4$ to $R^6$ or any one of $R^7$ to $R^9$, or at least one pair of any one of $R^{10}$ to $R^{12}$ and any one of $R^4$ to $R^6$ or any one of $R^7$ to $R^9$ may bond together to form a crosslinking substituent, or at least one pair of any one of $R^1$ to $R^3$ and any one of $R^4$ to $R^6$ or any one of $R^7$ to $R^9$ may bond together to form a crosslinking substituent, and at least one pair of any one of $R^{10}$ to $R^{12}$ and any one of $R^4$ to $R^6$ or any one of $R^7$ to $R^9$ may bond together to form a crosslinking substituent.

[5] The mononuclear ruthenium complex of [3] wherein $R^1$ to $R^6$ are each independently an alkyl, aryl or aralkyl group which may be substituted with X which is as defined above, L's are sulfides or thiols represented by $SR^{13}R^{14}$ and $SR^{15}R^{16}$ wherein $R^{13}$ to $R^{16}$ are each independently hydrogen or an alkyl, aryl or aralkyl group which may be substituted with X which is as defined above, at least one pair of either one of $R^{13}$ and $R^{14}$ and either one of $R^{15}$ and $R^{16}$ may bond together to form a crosslinking substituent.

[6] The mononuclear ruthenium complex of any one of [1] to [5] wherein a pair of any one of $R^1$ to $R^3$ and any one of $R^4$ to $R^6$ bond together to form a crosslinking substituent.

[7] The mononuclear ruthenium complex of [4] wherein any one of $R^1$ to $R^3$ and any one of $R^4$ to $R^6$ or any one of $R^7$ to $R^9$ bond together to form a crosslinking substituent, and any one of $R^{10}$ to $R^{12}$ and a substituent on Si which is selected from any one of $R^4$ to $R^6$ and any one of $R^7$ to $R^9$ and which does not participate in formation of said crosslinking substituent, bond together to form a crosslinking substituent.

[8] The mononuclear ruthenium complex of [5] or [6] wherein either one of $R^{13}$ and $R^{14}$ and either one of $R^{15}$ and $R^{16}$ bond together to form a crosslinking substituent.

[9] The mononuclear ruthenium complex of [7] wherein any one of $R^1$ to $R^3$ and any one of $R^4$ to $R^6$ bond together to form an o-phenylene group which may be substituted with Y, Y is hydrogen, halogen, $C_1$-$C_{10}$ alkyl, or $C_1$-$C_{10}$ alkoxy group, with the proviso that when a plurality of Y's are present, they may be the same or different, and any one of $R^{10}$ to $R^{12}$ and any one of $R^7$ to $R^9$ bond together to form an o-phenylene group which may be substituted with Y which is as defined above.

[10] The mononuclear ruthenium complex of [8] wherein any one of $R^1$ to $R^3$ and any one of $R^4$ to $R^6$ bond together to form an o-phenylene group which may be substituted with Y, Y is hydrogen, halogen, $C_1$-$C_{10}$ alkyl, or $C_1$-$C_{10}$ alkoxy group, with the proviso that when a plurality of Y's are present, they may be the same or different, and either one of $R^{13}$ and $R^{14}$ and either one of $R^{15}$ and $R^{16}$ bond together to form a $C_1$-$C_6$ alkylene group.

[11] A catalyst comprising the mononuclear ruthenium complex of any one of [1] to [10], the catalyst having activity to three reactions: hydrosilylation reaction, hydrogenation reaction, and reductive reaction of carbonyl compounds.

[12] A method for preparing an addition compound, comprising the step of effecting hydrosilylation reaction of a compound having an aliphatic unsaturated bond with a hydrosilane or organohydropolysiloxane having a Si—H bond in the presence of the catalyst of [11].

[13] A method for preparing an alkane compound, comprising the step of hydrogenating a compound having an aliphatic unsaturated bond in the presence of the catalyst of [11].

[14] A method for preparing an amine compound, comprising the step of reducing an amide compound with a silane or organohydropolysiloxane having a Si—H bond in the presence of the catalyst of [11].

[15] A method for preparing an alcohol compound, comprising the step of reducing an aldehyde, ketone or ester compound with a silane or organohydropolysiloxane having a Si—H bond in the presence of the catalyst of [11].

Advantageous Effects of Invention

When hydrosilylation reaction of an aliphatic unsaturated group-containing compound with a silane or polysiloxane having a Si—H group is carried out using a mononuclear ruthenium complex compound of the invention as the catalyst, addition reaction can occur under conditions from room temperature to 100° C. In particular, addition reaction with industrially useful polysiloxanes, and trialkoxysilanes and dialkoxysilanes takes place in an effective manner. Although the known documents indicate that in the relevant reaction, addition reaction to unsaturated group and dehydrogenation silylation reaction to form unsaturated group-containing compounds often take place concurrently, the use of the inventive catalyst ensures selective progress of addition reaction to unsaturated group. In the reaction with internal olefin, which is difficult with prior art catalysts, an addition reaction product can be formed concomitant with migration of unsaturated group to the terminal.

Hydrogenation reaction is possible under mild conditions including room temperature and atmospheric pressure of hydrogen gas. The catalyst is also effective for hydrogenation of multi-substituted alkenes which is difficult with prior art methods.

In reductive reaction of carbonyl compounds, amide, aldehyde, ketone and ester compounds may be reacted with silanes or polysiloxanes having a Si—H group which are easy to handle, thereby yielding the desired reduced compounds.

Another advantage of the complex compound of the invention is that a common complex compound displays high catalytic activity to a plurality of reactions including hydrosilylation reaction, hydrogenation reaction, and reductive reaction of carbonyl compounds. The complex compound is very useful in organic synthetic reactions.

DESCRIPTION OF EMBODIMENTS

Figure 1:
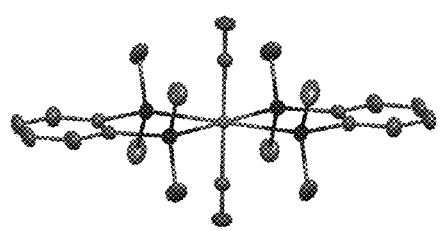
FIG. 1 illustrates the geometry of ruthenium complex A obtained in Example 1.

Now the invention is described in detail.
The invention provides a mononuclear ruthenium complex having Ru—Si bonds and having at least one carbon monoxide (CO) coordinated to Ru, as represented by formula (1).

[Chemical Formula 2]

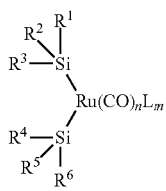

(1)

It is noted that in the mononuclear ruthenium complex of formula (1), when two CO's and two L's are contained (which are distinguishably represented by $L^1$ and $L^2$, respectively), for example, there exist coordination geometry isomers as depicted by the following formulae. The mononuclear ruthenium complex encompasses all such coordination geometry isomers.

[Chemical Formula 3]

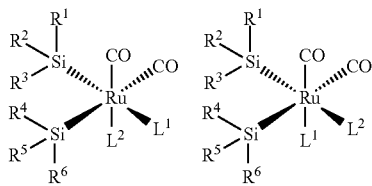

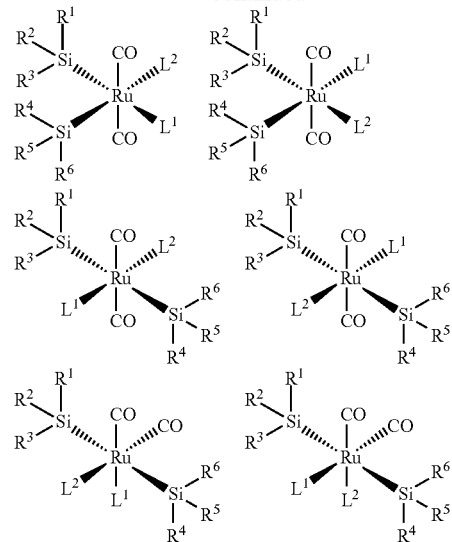

In the mononuclear ruthenium complex of the invention, carbon monoxide (CO) is an essential coordinate moiety to display catalytic activity. While n is an integer of 1 to 3, n is preferably equal to 1 or 2, most preferably 2 for further enhancement of catalytic activity.

$R^1$ to $R^6$ are each independently hydrogen, or an alkyl, aryl, aralkyl, organoxy, monoorganoamino, diorganoamino, monoorganophosphino, diorganophosphino, monoorganosilyl, diorganosilyl, triorganosilyl or organothio group which may be substituted with X, or at least one pair of any one of $R^1$ to $R^3$ and any one of $R^4$ to $R^6$, taken together, represent a crosslinking substituent, and X is a halogen atom, an organoxy, monoorganoamino, diorganoamino or organothio group.

The alkyl group may be straight, branched or cyclic. Although its carbon count is not particularly limited, alkyl groups of 1 to 30 carbons, more preferably 1 to 10 carbons are preferable. Examples include straight or branched alkyl groups such as methyl, ethyl, n-propyl, isopropyl, n-butyl, isobutyl, s-butyl, t-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-eicosanyl; and cycloalkyl groups such as cyclopropyl, cyclobutyl, cyclopentyl, cyclohexyl, cycloheptyl, cyclooctyl, and cyclononyl.

For the aryl group, aryl groups of 6 to 30 carbons, more preferably 6 to 20 carbons are preferable although the carbon count is not particularly limited. Examples include phenyl, 1-naphthyl, 2-naphthyl, anthryl, phenanthryl, o-biphenylyl, m-biphenylyl, and p-biphenylyl.

For the aralkyl group, aralkyl groups of 7 to 30 carbons, more preferably 7 to 20 carbons are preferable although the carbon count is not particularly limited. Examples include benzyl, phenylethyl, phenylpropyl, naphthylmethyl, naphthylethyl, and naphthylpropyl.

Suitable organooxy groups include, but are not limited to, alkoxy, aryloxy and aralkyloxy groups represented by RO wherein R is a substituted or unsubstituted $C_1$-$C_{30}$ alkyl group, $C_6$-$C_{30}$ aryl group or $C_7$-$C_{30}$ aralkyl group.

Suitable alkoxy group include, but are not limited to, alkoxy groups of 1 to 30 carbons, more preferably 1 to 10 carbons are preferable. Examples include methoxy, ethoxy, n-propoxy, i-propoxy, c-propoxy, n-butoxy, i-butoxy, s-butoxy, t-butoxy, n-pentoxy, n-hexoxy, n-heptyloxy, n-octyloxy, n-nonyloxy, and n-decyloxy.

Suitable aryloxy groups include, but are not limited to, aryloxy groups of 6 to 30 carbons, more preferably 6 to 20 carbons are preferable. Examples include phenoxy, 1-naphthyloxy, 2-naphthyloxy, anthryloxy, and phenanthryloxy.

Suitable aralkyloxy groups include, but are not limited to, aryloxy aralkyloxy groups of 7 to 30 carbons, more preferably 7 to 20 carbons are preferable. Examples include benzyloxy, phenylethyloxy, phenylpropyloxy, 1 or 2-naphthylmethyloxy, 1 or 2-naphthylethyloxy, 1 or 2-naphthylpropyloxy.

Suitable organothio groups include the foregoing organoxy groups whose oxygen atom is replaced by sulfur atom.

The monoorganoamino group is preferably a group of $RNH_2$ wherein R is as defined above, though not limited thereto. The preferred carbon count of R is the same as defined above for the alkoxy, aryloxy and aralkyloxy groups. Examples include straight or branched monoalkylamino groups such as methylamino, ethylamino, n-propylamino, isopropylamino, n-butylamino, isobutylamino, s-butylamino, t-butylamino, n-pentylamino, n-hexylamino, n-heptylamino, n-octylamino, n-nonylamino, n-decylamino, n-undecylamino, n-dodecylamino, n-tridecylamino, n-tetradeylamino, n-pentadecylamino, n-hexadecylamino, n-heptadecylamino, n-octadecylamino, n-nonadecylamino, and n-eicosanylamino; monocycloalkylamino groups such as cyclopropylamino, cyclobutylamino, cyclopentylamino, cyclohexylamino, cycloheptylamino, cyclooctylamino, and cyclononylamino; monoarylamino groups such as anilino, 1 or 2-naphthylamino; and monoaralkylamino groups such as benzylamino, phenylethylamino, phenylpropylamino, 1 or 2-naphthylmethylamino.

The diorganoamino group is preferably a group of $R_2NH$ wherein R is independently as defined above, though not limited thereto. The preferred carbon count of R is the same as defined above for the alkoxy, aryloxy and aralkyloxy groups. Examples include straight or branched dialkylamino groups such as dimethylamino, diethylamino, di-n-propylamino, diisopropylamino, di-n-butylamino, diisobutylamino, di-s-butylamino, di-t-butylamino, di-n-pentylamino, di-n-hexylamino, di-n-heptylamino, di-n-octylamino, di-n-nonylamino, di-n-decylamino, di-n-undecylamino, di-n-dodecylamino, di-n-tridecylamino, di-n-tetradeylamino, di-n-pentadecylamino, di-n-hexadecylamino, di-n-heptadecylamino, di-n-octadecylamino, di-n-nonadecylamino, di-n-eicosanylamino, N-ethylmethylamino, N-isopropylmethylamino, and N-butylmethylamino; dicycloalkylamino groups such as dicyclopropylamino, dicyclobutylamino, dicyclopentylamino, dicyclohexylamino, dicycloheptylamino, dicyclooctylamino, dicyclononylamino, and cyclopentylcyclohexylamino; alkylarylamino groups such as N-methylanilino, N-ethylanilino, and N-n-propylanilino; diarylamino groups such as diphenylamino, 4,4'-bisnaphthylamino, N-phenyl-1 or 2-naphthylamino; and diaralkylamino groups such as dibenzylamino, bis(phenylethyl)amino, bis(phenylpropyl)amino, bis(1 or 2-naphthylmethyl)amino.

The monoorganophosphino group is preferably a group of RPH wherein R is independently as defined above, though not limited thereto. The preferred carbon count of R is the same as defined above for the alkoxy, aryloxy and aralkyloxy groups. Examples include straight or branched monoalkylphosphino groups such as methylphosphino, ethylphosphino, n-propylphosphino, isopropylphosphino, n-butylphosphino, isobutylphosphino, s-butylphosphino, t-butylphosphino, n-pentylphosphino, n-hexylphosphino, n-heptylphosphino, n-octylphosphino, n-nonylphosphino, n-decylphosphino, n-undecylphosphino, n-dodecylphosphino, n-tridecylphosphino, n-tetradeylphosphino, n-pentadecylphosphino, n-hexadecylphosphino, n-heptadecylphosphino, n-octadecylphosphino, n-nonadecylphosphino, and n-eicosanylphosphino; monocycloalkylphosphino groups such as cyclopropylphosphino, cyclobutylphosphino, cyclopentylphosphino, cyclohexylphosphino, cycloheptylphosphino, cyclooctylphosphino, and cyclononylphosphino; monoarylphosphino groups such as phenylphosphino, 1 or 2-naphthylphosphino; and monoaralkylphosphino groups such as benzylphosphino.

The diorganophosphino group is preferably a group of $R_2P$ wherein R is independently as defined above, though not limited thereto. The preferred carbon count of R is the same as defined above for the alkoxy, aryloxy and aralkyloxy groups. Examples include straight or branched dialkylphosphino groups such as dimethylphosphino, diethylphosphino, di-n-propylphosphino, diisopropylphosphino, di-n-butylphosphino, diisobutylphosphino, di-s-butylphosphino, di-t-butylphosphino, di-n-pentylphosphino, di-n-hexylphosphino, di-n-heptylphosphino, di-n-octylphosphino, di-n-nonylphosphino, di-n-decylphosphino, di-n-undecylphosphino, di-n-dodecylphosphino, di-n-tridecylphosphino, di-n-tetradeylphosphino, di-n-pentadecylphosphino, di-n-hexadecylphosphino, di-n-heptadecylphosphino, di-n-octadecylphosphino, di-n-nonadecylphosphino, and di-n-eicosanylphosphino; dicycloalkylphosphino groups such as dicyclopropylphosphino, dicyclobutylphosphino, dicyclopentylphosphino, dicyclohexylphosphino, dicycloheptylphosphino, dicyclooctylphosphino, and dicyclononylphosphino; alkylarylphosphino groups such as cyclohexylphenylphosphino; diarylphosphino groups such as diphenylphosphino, bis(1 or 2-naphthyl)phosphino; and diaralkylphosphino groups such as dibenzylphosphino, bis(phenylethyl)phosphino, bis(1 or 2-naphthylmethyl)phosphino.

The monoorganosilyl group is preferably a group of $RSiH_2$ wherein R is as defined above, though not limited thereto. The preferred carbon count of R is the same as defined above for the alkoxy, aryloxy and aralkyloxy groups. Examples include straight or branched monoalkylsilyl groups such as methylsilyl, ethylsilyl, n-propylsilyl, isopropylsilyl, n-butylsilyl, isobutylsilyl, s-butylsilyl, t-butylsilyl, n-pentylsilyl, n-hexylsilyl, n-heptylsilyl, n-octylsilyl, n-nonylsilyl, n-decylsilyl, n-undecylsilyl, n-dodecylsilyl, n-tridecylsilyl, n-tetradeylsilyl, n-pentadecylsilyl, n-hexadecylsilyl, n-heptadecylsilyl, n-octadecylsilyl, n-nonadecylsilyl, and n-eicosanylsilyl; monocycloalkylsilyl groups such as cyclopropylsilyl, cyclobutylsilyl, cyclopentylsilyl, cyclohexylsilyl, cycloheptylsilyl, cyclooctylsilyl, and cyclononylsilyl; monoarylsilyl groups such as phenylsilyl, 1 or 2-naphthylsilyl; and monoaralkylsilyl groups such as benzylsilyl, phenylethylsilyl, phenylpropylsilyl, 1 or 2-naphthylmethylsilyl.

The diorganosilyl group is preferably a group of $R_2SiH$ wherein R is independently as defined above, though not limited thereto. The preferred carbon count of R is the same as defined above for the alkoxy, aryloxy and aralkyloxy groups. Examples include straight or branched dialkylsilyl groups such as dimethylsilyl, diethylsilyl, di-n-propylsilyl, diisopropylsilyl, di-n-butylsilyl, diisobutylsilyl, di-s-butylsilyl, di-t-butylsilyl, di-n-pentylsilyl, di-n-hexylsilyl, di-n-heptylsilyl, di-n-octylsilyl, di-n-nonylsilyl, di-n-decylsilyl, di-n-undecylsilyl, di-n-dodecylsilyl, di-n-tridecylsilyl, di-n-tetradeylsilyl, di-n-pentadecylsilyl, di-n-hexadecylsilyl, di-n-heptadecylsilyl, di-n-octadecylsilyl, di-n-nonadecylsilyl, di-n-eicosanylsilyl, ethylmethylsilyl, isopropylmethylsilyl, and butylmethylsilyl; dicycloalkylsilyl groups such as dicyclopropylsilyl, dicyclobutylsilyl, dicyclopentylsilyl, dicyclohexylsilyl, dicycloheptylsilyl, dicyclooctylsilyl, dicyclononylsilyl, and cyclopentylcyclohexylsilyl; alkylarylsilyl groups such as methylphenylsilyl, ethylphenylsilyl, and n-propylphenylsilyl; diarylsilyl groups such as diphenylsilyl, bis(1 or 2-naphthyl)silyl, phenyl-1 or 2-naphthylsilyl; and diaralkylsilyl groups such as dibenzylsilyl, bis(phenylethyl)silyl, bis(phenylpropyl)silyl, bis(1 or 2-naphthylmethyl)silyl.

The triorganosilyl group is preferably a group of $R_3Si$ wherein R is independently as defined above, though not limited thereto. The preferred carbon count of R is the same as defined above for the alkoxy, aryloxy and aralkyloxy groups. Examples include straight or branched trialkylsilyl groups such as trimethylsilyl, triethylsilyl, tri-n-propylsilyl, triisopropylsilyl, tri-n-butylsilyl, triisobutylsilyl, tri-s-butylsilyl, tri-t-butylsilyl, tri-n-pentylsilyl, tri-n-hexylsilyl, tri-n-heptylsilyl, tri-n-octylsilyl, tri-n-nonylsilyl, tri-n-decylsilyl, tri-n-undecylsilyl, tri-n-dodecylsilyl, tri-n-tridecylsilyl, tri-n-tetradeylsilyl, tri-n-pentadecylsilyl, tri-n-hexadecylsilyl, tri-n-heptadecylsilyl, tri-n-octadecylsilyl, tri-n-nonadecylsilyl, tri-n-eicosanylsilyl, tri-n-eicosanylsilyl, ethyldimethylsilyl, diisopropylmethylsilyl, and dibutylmethylsilyl; tricycloalkylsilyl groups such as tricyclopropylsilyl, tricyclobutylsilyl, tricyclopentylsilyl, tricyclohexylsilyl, tricycloheptylsilyl, tricyclooctylsilyl, and tricyclononylsilyl; alkylarylsilyl groups such as methyldiphenylsilyl, ethyldiphenylsilyl, and n-propyldiphenylsilyl; triarylsilyl groups such as triphenylsilyl, tri(1 or 2-naphthyl)silyl, diphenyl-1 or 2-naphthylsilyl; and triaralkylsilyl groups such as tribenzylsilyl, tri(phenylethyl)silyl, tri(phenylpropyl)silyl, tri(1 or 2-naphthylmethyl)silyl.

With respect to the foregoing substituent groups, at least one hydrogen atom on R may be substituted by a substituent X. Suitable substituents X include halogen, organoxy, monoorganoamino, diorganoamino, and organothio groups, and examples of the organoxy, monoorganoamino, diorganoamino, and organothio groups are as exemplified above.

Exemplary of the halogen are fluorine, chlorine, bromine and iodine, with fluorine being preferred. Suitable fluorine-substituted alkyl groups include trifluoropropyl, nonafluorohexyl and heptadecylfluorodecyl.

Of the foregoing substituent groups, $R^1$ to $R^6$ are each independently selected preferably from $C_1$-$C_{30}$ alkyl, $C_6$-$C_{30}$ aryl, and $C_7$-$C_{30}$ aralkyl groups which may be substituted with X, more preferably from $C_1$-$C_{10}$ alkyl and $C_6$-$C_{10}$ aryl groups.

When a pair of any one of $R^1$ to $R^3$ and any one of $R^4$ to $R^6$, taken together, represent a crosslinking substituent, the crosslinking substituent is not particularly limited as long as it is capable of crosslinking two silicon atoms. Exemplary crosslinking substituents include —O—, —S—, —NH—, —NR— wherein R is as defined above, —PR— wherein R is as defined above, —NH—$(CH_2)_k$—NH— wherein k is an integer of 1 to 10, —NR—$(CH_2)_k$—NR— wherein k is as defined above and R is independently as defined above, —PH—$(CH_2)_k$—PH— wherein k is as defined above, —PR—$(CH_2)_k$—PR— wherein k is as defined above and R is independently as defined above, —C═C—, $C_1$-$C_{10}$ alkylene, $C_6$-$C_{30}$ arylene, $C_7$-$C_{30}$ aralkylene, —$(CH_2O)_k$— wherein k is as defined above, —$(CH_2O)_k$—O—$(CH_2O)_k$— wherein k is independently as defined above, —O—$(CH_2O)_k$—O— wherein k is as defined above, —R'—O—$(CH_2O)_k$—O—R'— wherein R' is each independently a $C_1$-$C_{10}$ alkylene group, $C_6$-$C_{30}$ arylene group or $C_7$-$C_{30}$ aralkylene group and k is as defined above, —$(CH_2S)_k$— wherein k is as defined above, —$(CH_2)_k$—S—$(CH_2)_k$— wherein k is independently as defined above, —S—$(CH_2)_k$—S— wherein k is as defined above, —R'—S—$(CH_2)_k$—O—R'— wherein R' is independently as defined above and k is as defined above, —$SiR_2$— wherein R is independently as defined above, and —$(CH_2)_k$—$SiR_2$—$(CH_2)_k$— wherein R is independently as defined above and k is independently as defined above.

Suitable $C_1$-$C_{10}$ alkylene groups include methylene, ethylene, propylene, trimethylene, tetramethylene, pentamethylene, and hexamethylene.

Suitable $C_6$-$C_{30}$ arylene groups include o-phenylene(1,2-phenylene), 1,2-naphthylene, 1,8-naphthylene, and 2,3-naphthylene.

Suitable $C_7$-$C_{30}$ aralkylene groups include —$(CH_2)_k$—Ar— wherein Ar is a $C_6$-$C_{20}$ arylene group and k is as defined above, —Ar—$(CH_2)_k$— wherein Ar and k are as defined above, and —$(CH_2)_k$—Ar—$(CH_2)_k$— wherein Ar is as defined above and k is independently as defined above.

Notably, in the foregoing alkylene, arylene and aralkylene groups, at least one hydrogen atom may be substituted by a substituent X wherein X is as defined above.

Assume that Z stands for a crosslinking substituent. Since the number of Z linking two silicon atoms is 1 to 3, the mononuclear ruthenium complex having a crosslinking substituent Z is represented by the following formulae.

[Chemical Formula 4]

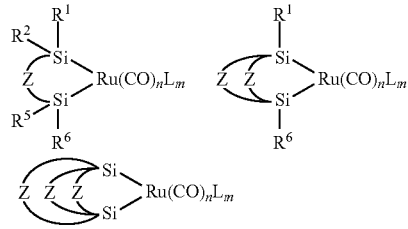

Herein $R^1$, $R^2$, $R^5$, $R^6$, L, n and m are as defined above, and Z is a crosslinking substituent.

Illustrative examples of the disilametallacycle structure having a crosslinking substituent include those of the following formulae, but are not limited thereto.

[Chemical Formula 5]

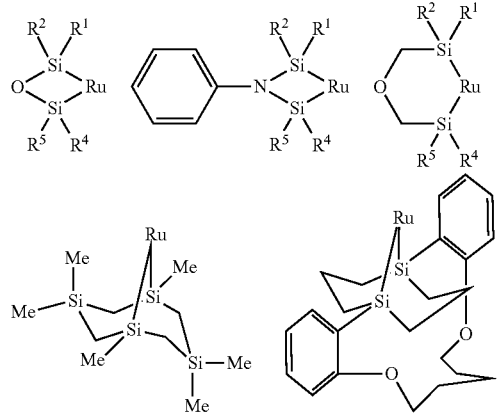

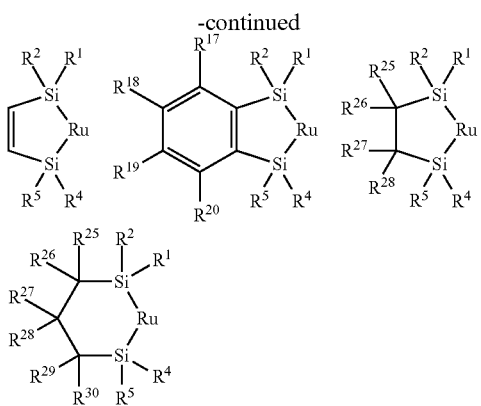

Herein Me stands for methyl.

In the above formulae, $R^1$, $R^2$, $R^4$ and $R^5$ are as defined above, $R^{17}$ to $R^{20}$ (substituent Y) are each independently hydrogen, halogen, $C_1$-$C_{10}$ alkyl, or $C_1$-$C_{10}$ alkoxy group, $R^{25}$ to $R^{30}$ are each independently hydrogen or a substituted or unsubstituted, $C_1$-$C_{20}$ monovalent hydrocarbon group. Preferably $R^{17}$ to $R^{20}$ and $R^{25}$ to $R^{30}$ are hydrogen.

Suitable monovalent hydrocarbon groups include alkyl, aryl and aralkyl groups, examples of which are as exemplified above.

Examples of the alkyl group, alkoxy group and halogen are as exemplified above.

L is a two-electron ligand other than CO and phosphine, wherein two electrons coordinate with ruthenium.

The two-electron ligand is not particularly limited as long as CO and phosphine are excluded. Use may be made of any ligands which are conventionally used as the two-electron ligand in metal complexes, exclusive of CO. Typical ligands include compounds of nitrogen, oxygen, sulfur, and other elements containing an unshared electron pair (unpaired electron) such as amine, imine, nitrogen-containing heterocycle, arsine, alcohol, thiol, ether, and sulfide; compounds containing π-electron such as alkene and alkyne; compounds containing both unpaired electron and π-electron such as aldehyde, ketone, nitrile, and isonitrile; molecular hydrogen (σ-electron in H—H bond coordinates) and hydrosilane (σ-electron in Si—H bond coordinates) capable of bonding by agostic interaction.

Included in the amine are tertiary amines represented by $R_3N$ wherein R is each independently as defined above.

Included in the imine are those represented by RC(=NR)R wherein R is each independently as defined above.

Examples of the nitrogen-containing heterocycle include pyrrole, imidazole, pyridine, pyrimidine, oxazoline, and isooxazoline.

Examples of the arsine include those of $R_3As$ wherein R is each independently as defined above.

Examples of the alcohol include those of ROH wherein R is as defined above.

Included in the thiol are those obtained by substituting sulfur atom for oxygen atom of the above alcohols.

Included in the ether are those represented by ROR wherein R is each independently as defined above.

Included in the sulfide are those obtained by substituting sulfur atom for oxygen atom of the above ethers.

Included in the ketone are those represented by RCOR wherein R is each independently as defined above.

Included in the isonitrile are those represented by RNC wherein R is each independently as defined above.

Included in the alkene are those of 2 to 30 carbon atoms such as ethene, propene, 1-butene, 2-butene, 1-pentene, 2-pentene, cyclopentene, 1-hexene, cyclohexene, 1-heptene, 1-octene, 1-nonene, and 1-decene.

Included in the alkyne are those of 2 to 30 carbon atoms such as ethyne, propyne, 1-butyne, 2-butyne, 1-pentyne, 2-pentyne, 1-hexyne, 1-heptyne, 1-octyne, 1-nonyne, and 1-decyne.

Examples of the hydrosilane include triorganohydrosilanes, specifically tri($C_1$-$C_{30}$ organo)hydrosilanes, for example, those of $R^1R^2R^3SiH$ wherein $R^1$ to $R^3$ are as defined above.

Of the foregoing, the two-electron ligand L is preferably molecular hydrogen, amine, imine, nitrogen-containing heterocycle, arsine, alcohol, thiol, ether, sulfide, nitrile, isonitrile, aldehyde, ketone, $C_2$-$C_{30}$ alkene, $C_2$-$C_{30}$ alkyne, or triorganohydrosilane.

Where two L's are present, they may bond together to form a ligand containing two coordinating two-electron functional groups. Typical examples include, but are not limited to, ethylenediamine, ethylene glycol dimethyl ether, 1,3-butadiene, and those of the formulae shown below.

In the mononuclear ruthenium complex, it is excluded that where three L's are present, all they bond together to form a ligand containing three coordinating two-electron functional groups.

[Chemical Formula 6]

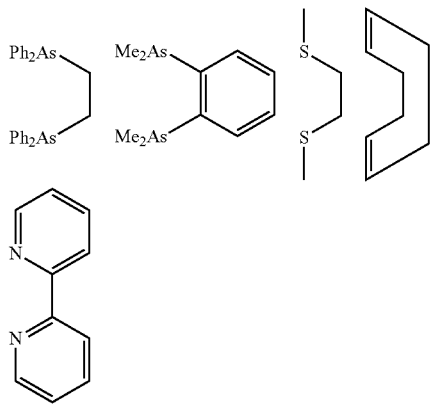

Herein Me stands for methyl, and Ph for phenyl.

In the mononuclear ruthenium complex, the coordination number m of two-electron ligand L is an integer of 1 to 3, preferably 2.

The sum of the coordination number n of CO and the coordination number m of L is equal to 3 or 4, preferably 4.

Herein, a two-electron ligand L which forms a relatively weak bond with ruthenium is advantageous in terms of catalytic activity. Among the above examples, L is more preferably a thiol, sulfide, or triorganohydrosilane, and even more preferably two triorganohydrosilanes of $SiHR^7R^8R^9$ and $SiHR^{10}R^{11}R^{12}$ wherein $R^7$ to $R^{12}$ are each independently an alkyl, aryl or aralkyl group which may be substituted with X which is as defined above, and two sulfides or thiols of $SR^{13}R^{14}$ and $SR^{15}R^{16}$ wherein $R^{13}$ to $R^{16}$ are each independently hydrogen, or an alkyl, aryl or aralkyl group which may be substituted with X which is as defined above.

Examples of the alkyl, aryl and aralkyl group are the same as exemplified above, while $C_1$-$C_{10}$ alkyl, $C_6$-$C_{20}$ aryl and $C_7$-$C_{20}$ aralkyl groups are preferred, and $C_1$-$C_{10}$ alkyl and $C_6$-$C_{20}$ aryl groups are more preferred.

When L's are triorganohydrosilanes of $SiHR^7R^8R^9$ and $SiHR^{10}R^{11}R^{12}$ wherein $R^7$ to $R^{12}$ are as defined above, at least two of four silicon atoms in the mononuclear ruthenium complex may be linked by the crosslinking substituent Z. A combination of silicon atoms may be either a combination of silicon atoms having a silicon-ruthenium covalent bond, a combination of silicon atoms in Si—H coordination, or a combination of a silicon-ruthenium covalent bond with a silicon atom in Si—H coordination. Herein, the number of Z linking two silicon atoms is 1 to 3 whereas the total number of Z in the overall complex is 1 to 12.

When a mononuclear ruthenium complex having crosslinking substituent Z is represented by a single coordination geometry, exemplary geometries are those of the following formulae, but not limited thereto. As alluded to previously, there are present coordination geometry isomers other than the illustrated ones, and in such cases, similar geometries having crosslinking substituent Z are present.

[Chemical Formula 7]

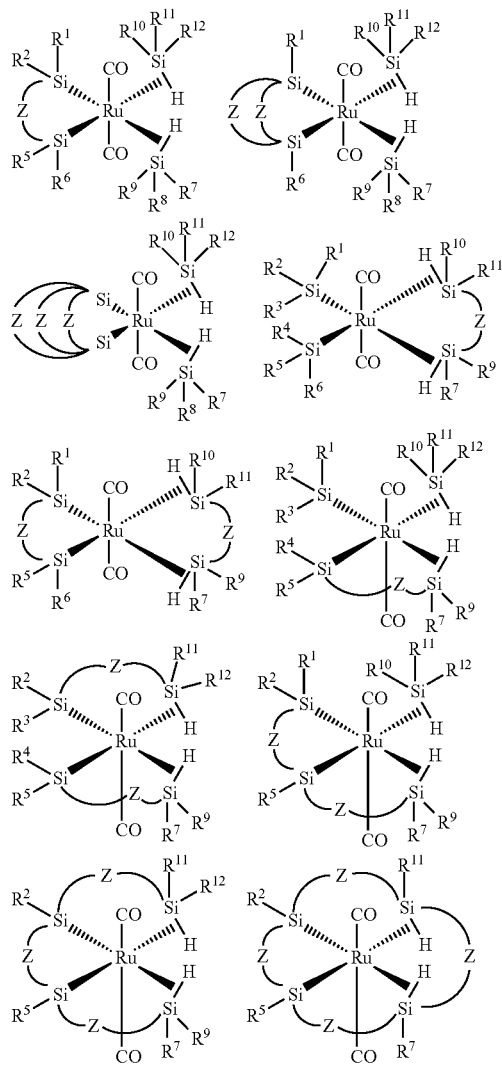

Herein $R^1$ to $R^{12}$ and Z are as defined above.

Exemplary geometries of the mononuclear ruthenium complex having disilametallacycle structure include those of the following formulae (depicted with CO omitted), but are not limited thereto.

[Chemical Formula 8]

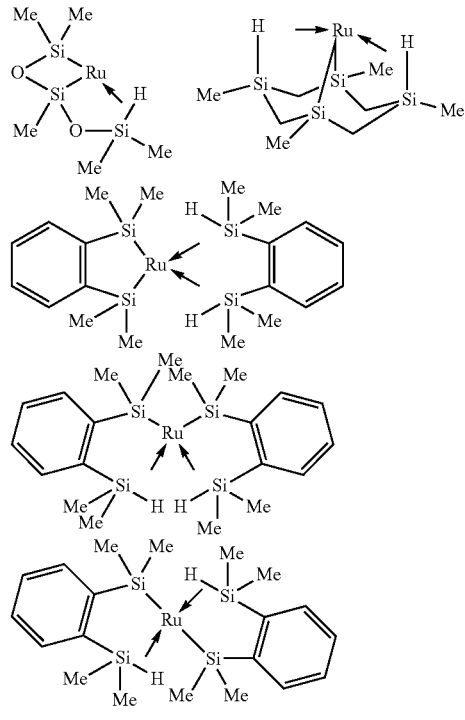

Herein Me stands for methyl.

When L's are two sulfides or thiols of $SR^{13}R^{14}$ and $SR^{15}R^{16}$ wherein $R^{13}$ to $R^{16}$ are as defined above, two sulfur atoms in the mononuclear ruthenium complex may be linked by the crosslinking substituent Z.

When a mononuclear ruthenium complex having crosslinking substituent Z is represented by a single coordination geometry, exemplary geometries are those of the following formulae, but not limited thereto. As alluded to previously, there are present coordination geometry isomers other than the illustrated ones, and in such cases, similar geometries having crosslinking substituent Z are present.

In these cases, two silicon atoms in the mononuclear ruthenium complex may be linked by the crosslinking substituent Z.

[Chemical Formula 9]

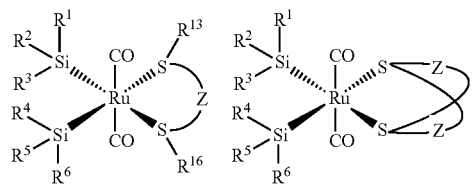

Herein $R^1$ to $R^6$, $R^{13}$, $R^{16}$ and Z are as defined above.

Exemplary geometries of the dithia(dithio)metallacycle structure include those of the following formulae, but are not limited thereto.

[Chemical Formula 10]

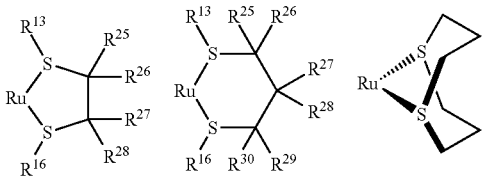

Herein $R^{13}$, $R^{16}$, $R^{25}$ to $R^{30}$ are as defined above.

Exemplary geometries of the mononuclear ruthenium complex having dithiametallacycle structure include those of the following formulae, but are not limited thereto.

[Chemical Formula 11]

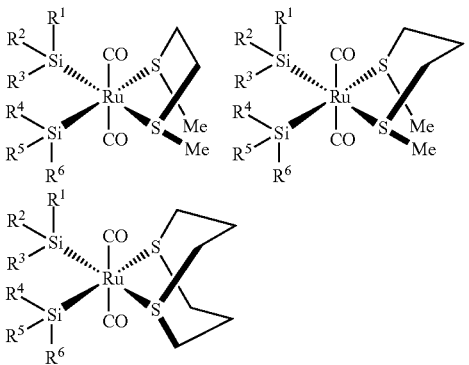

Herein $R^1$ to $R^6$ are as defined above and Me stands for methyl.

Especially preferred in the invention are mononuclear ruthenium complexes having two CO's coordinated and triorganohydrosilanes (as two-electron ligand) in agostic Si—H bond coordination. When such a ruthenium complex is represented for convenience sake by a single coordination geometry, exemplary geometries are those of formula (2). As alluded to previously, other coordination geometry isomers are acceptable.

[Chemical Formula 12]

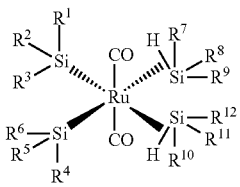

(2)

Herein $R^1$ to $R^{12}$ are as defined above. Preferably $R^1$ to $R^6$ are each independently an alkyl, aryl or aralkyl group which may be substituted with X which is as defined above.

Examples of the alkyl, aryl and aralkyl groups are the same as exemplified above, while $C_1$-$C_{10}$ alkyl, $C_6$-$C_{20}$ aryl and $C_7$-$C_{20}$ aralkyl groups are preferred, and $C_1$-$C_{10}$ alkyl and $C_6$-$C_{20}$ aryl groups are more preferred.

In formula (2) as well, at least two of four silicon atoms in the mononuclear ruthenium complex may be linked by the crosslinking substituent. Specifically, at least one pair of any one of $R^1$ to $R^3$ and any one of $R^4$ to $R^6$ or any one of $R^7$ to $R^9$, or at least one pair of any one of $R^{10}$ to $R^{12}$ and any one of $R^4$ to $R^6$ or any one of $R^7$ to $R^9$ may bond together to form a crosslinking substituent such as alkylene, arylene or aralkylene. Alternatively, at least one pair of any one of $R^1$ to $R^3$ and any one of $R^4$ to $R^6$ or any one of $R^7$ to $R^9$ may bond together to form a crosslinking substituent such as alkylene, arylene or aralkylene, and at least one pair of any one of $R^{10}$ to $R^{12}$ and any one of $R^4$ to $R^6$ or any one of $R^7$ to $R^9$ may bond together to form a crosslinking substituent such as alkylene, arylene or aralkylene.

Examples of the alkylene, arylene and aralkylene groups are the same as exemplified above, while $C_1$-$C_{10}$ alkylene, $C_7$-$C_{20}$ arylene and $C_7$-$C_{20}$ aralkylene groups are preferred, and $C_1$-$C_6$ alkylene and $C_7$-$C_{20}$ arylene groups are more preferred.

Also useful are mononuclear ruthenium complexes having two CO's coordinated and two sulfides or thiols (as two-electron ligand) coordinated. When such a ruthenium complex is represented for convenience sake by a single coordination geometry, exemplary geometries are those of formula (3). As alluded to previously, other coordination geometry isomers are acceptable.

[Chemical Formula 13]

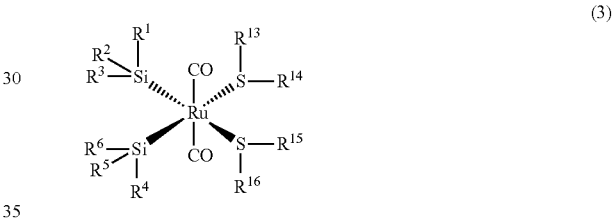

(3)

In formula (3), $R^1$ to $R^6$ and $R^{13}$ to $R^{16}$ are as defined above. Preferably $R^{13}$ to $R^{16}$ are each independently an alkyl, aryl or aralkyl group which may be substituted with X which is as defined above.

Examples of the alkyl, aryl and aralkyl groups are the same as exemplified above, while $C_1$-$C_{10}$ alkyl, $C_6$-$C_{20}$ aryl and $C_7$-$C_{20}$ aralkyl groups are preferred, and $C_1$-$C_{10}$ alkyl and $C_6$-$C_{20}$ aryl groups are more preferred.

In formula (3) as well, two sulfur atoms in the mononuclear ruthenium complex may be linked by the crosslinking substituent. Specifically, at least one pair of either one of $R^{13}$ and $R^{14}$ and either one of $R^{15}$ and $R^{16}$ may bond together to form a crosslinking substituent such as alkylene, arylene or aralkylene.

In this case, two silicon atoms in the mononuclear ruthenium complex may be linked by the crosslinking substituent. Specifically, at least one pair of any one of $R^1$ to $R^3$ and any one of $R^4$ to $R^6$ may bond together to form a crosslinking substituent such as alkylene, arylene or aralkylene.

Examples of the alkylene, arylene and aralkylene groups are the same as exemplified above, while $C_1$-$C_{10}$ alkylene, $C_7$-$C_{20}$ arylene and $C_7$-$C_{20}$ aralkylene groups are preferred, and $C_1$-$C_6$ alkylene and $C_7$-$C_{20}$ arylene groups are more preferred.

When the preferred mononuclear ruthenium complex which can be used herein is represented by a single coordination geometry, exemplary geometries are those of formulae (4) and (5), more specifically formulae (6) and (7). As alluded to previously, other coordination geometry isomers are acceptable.

[Chemical Formula 14]

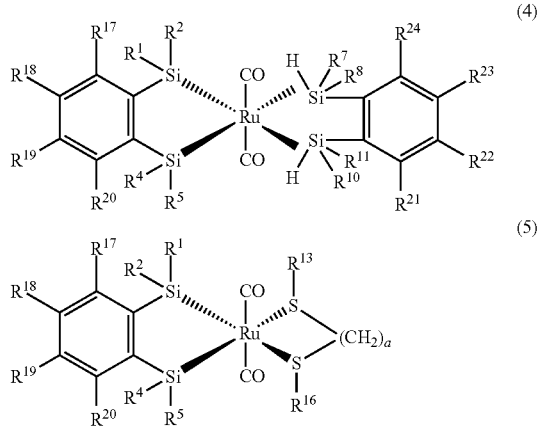

Herein, $R^1$, $R^2$, $R^4$, $R^5$, $R^7$, $R^8$, $R^{10}$, $R^{11}$, $R^{13}$, and $R^{16}$ to $R^{20}$ are as defined above, and $R^{21}$ to $R^{24}$ are as defined for $R^{17}$.

In formula (5), "a" is an integer of 1 to 6, preferably 2 or 3.

[Chemical Formula 15]

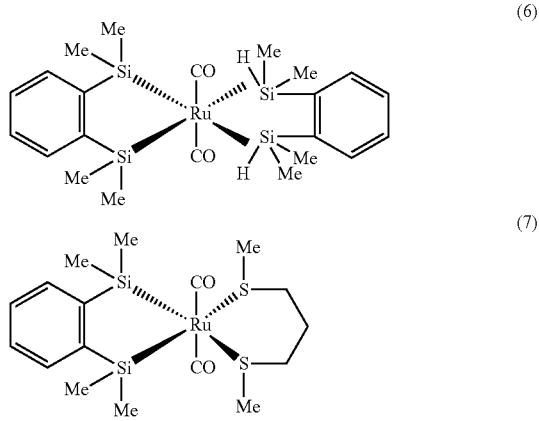

Herein Me stands for methyl.

The mononuclear ruthenium complex of the invention may be prepared by any combination of well-known organic synthetic reactions.

For example, the ruthenium complex having formula (4) or (6) may be obtained by irradiating with light a ruthenium-carbonyl complex having a cycloalkadienyl group such as cyclohexadienyl or cyclooctadienyl as a ligand and a bissilyl compound such as 1,2-bis(dimethylsilyl)benzene in an inert gas atmosphere such as argon gas.

In this case, the amount of the bissilyl compound used may be about 1 to 10 moles, preferably 2 to 5 moles per mole of the ruthenium-carbonyl complex.

As the organic solvent, any solvents may be used as long as they do not adversely affect the reaction. Suitable solvents used herein include aliphatic hydrocarbons such as pentane, hexane, heptane, octane, and cyclohexane; ethers such as diethyl ether, diisopropyl ether, dibutyl ether, cyclopentyl methyl ether, tetrahydrofuran, and 1,4-dioxane; and aromatic hydrocarbons such as benzene, toluene, xylene and mesitylene.

The reaction temperature may be set as appropriate in the range from the melting point to the boiling point of the organic solvent, preferably in the range of 10 to 50° C., and more preferably 15 to 30° C.

The reaction time is typically about 1 to about 48 hours.

After the completion of reaction, the solvent is distilled off, whereupon the target compound may be isolated by well-known purifying means such as recrystallization. Without isolation, the ruthenium complex as prepared may be used as a catalyst for the intended reaction.

Also, the ruthenium complex having a sulfide ligand as represented by formula (5) or (7) may be prepared by starting with the ruthenium complex of formula (4) or (6) obtained by the above method, for example, and reacting it with a dithia hydrocarbon compound (e.g., 2,6-dithiaheptane) or a thiol compound (e.g., 1,3-propanedithiol) in an organic solvent as exemplified above in an inert gas atmosphere such as argon gas.

In this case, the amount of the dithia hydrocarbon compound used may be about 1 to 3 moles, preferably 1 to 1.5 moles, and more preferably 1 to 1.2 moles per mole of the ruthenium complex.

The reaction temperature may be set as appropriate in the range from 0° C. to the boiling point of the organic solvent, preferably in the range of 10 to 50° C., and more preferably 15 to 30° C.

The reaction time is typically about 1 to about 48 hours.

After the completion of reaction, the solvent is distilled off, whereupon the target compound may be isolated by well-known purifying means such as recrystallization. Without isolation, the ruthenium complex as prepared may be used as a catalyst for the intended reaction.

As alluded to previously, the mononuclear ruthenium complex of the invention displays catalytic activity to three reactions: hydrosilylation reaction, hydrogenation reaction, and reductive reaction of carbonyl compounds.

For hydrosilylation reaction between a compound having an aliphatic unsaturated bond such as an olefin, silane or organopolysiloxane compound and a compound having a Si—H bond such as a silane or organopolysiloxane compound in the presence of the inventive mononuclear ruthenium complex as catalyst, the amount of the catalyst used, though not particularly limited, is preferably at least 0.5 mol % when it is taken into account that the target compound is obtained in high yields by driving reaction under mild conditions at room temperature to about 100° C.

When an olefin compound having an aliphatic unsaturated bond is reduced with hydrogen gas in the presence of the inventive mononuclear ruthenium complex as catalyst, to produce a saturated compound, the amount of the catalyst used, though not particularly limited, is preferably at least 1 mol % when it is taken into account that the target compound is obtained in high yields by driving reaction under mild conditions at room temperature and a hydrogen pressure of about 1 atm.

In either of the reactions, the upper limit of the amount of the catalyst used is about 10 mol % from the economic aspect, though not critical.

Also, when a carbonyl compound is reduced with a silane or siloxane compound having a Si—H group in the presence of the inventive mononuclear ruthenium complex as catalyst, the amount of the catalyst used, though not particularly limited, is preferably at least 0.01 mol % when it is taken into account that the target compound is obtained in high yields by driving reaction under mild conditions. The upper limit of the amount of the catalyst used is about 5 mol % from the economic aspect, though not critical.

Examples of the carbonyl compound which can be subjected to reductive reaction include compounds having an amide, aldehyde, ketone, ester, carboxylic acid, and carboxylic acid salt (e.g., sodium or potassium salt) group. The carbonyl compound can be converted to a corresponding amine or alcohol compound by reacting it with a silane or siloxane having a Si—H group in the presence of the inventive ruthenium complex catalyst.

EXAMPLES

Examples of the invention are given below by way of illustration and not by way of limitation.

For synthesis of ruthenium complexes, a Schlenk system or glovebox was used, and all steps were performed in nitrogen or argon atmosphere. All the solvents used in the preparation of transition metal compounds were deoxygenated and dried by well-known techniques prior to use.

Hydrosilylation reaction of alkene, reductive reaction of amide, and solvent purification were all performed in an inert gas atmosphere. All the solvents and ingredients used in these reactions were purified, dried and deoxygenated by well-known techniques prior to use.

Analysis of $^1$H, $^{13}$C and $^{29}$Si-NMR was performed by JNM-ECA600 and JNM-LA400 (JEOL Ltd.); IR spectroscopy by FT/IR-550 (JASCO Corp.); elemental analysis by 2400II/CHN (Perkin Elmer); X-ray crystallography by Vari-Max (Rigaku Corp.) with MoK α-ray of 0.71069 angstrom.

It is noted that in the chemical structural formulae shown below, hydrogen atoms are omitted according to the standard nomenclature. Me stands for methyl.

(1) Synthesis of Ruthenium Complex

Example 1

Synthesis of Ruthenium Complex A

Figure 2:
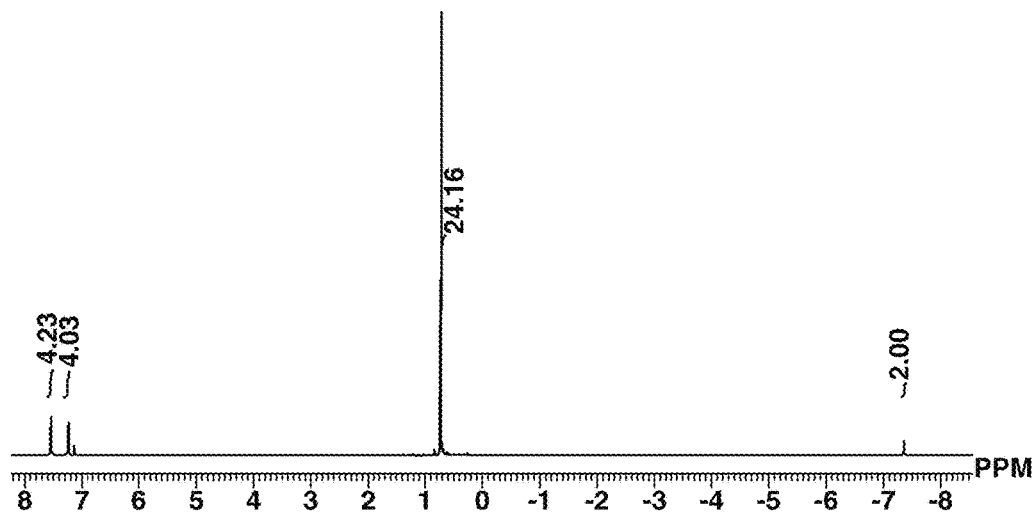
FIG. 2 is a diagram showing $^1$H-NMR spectrum of ruthenium complex A in Example 1.
Figure 3:
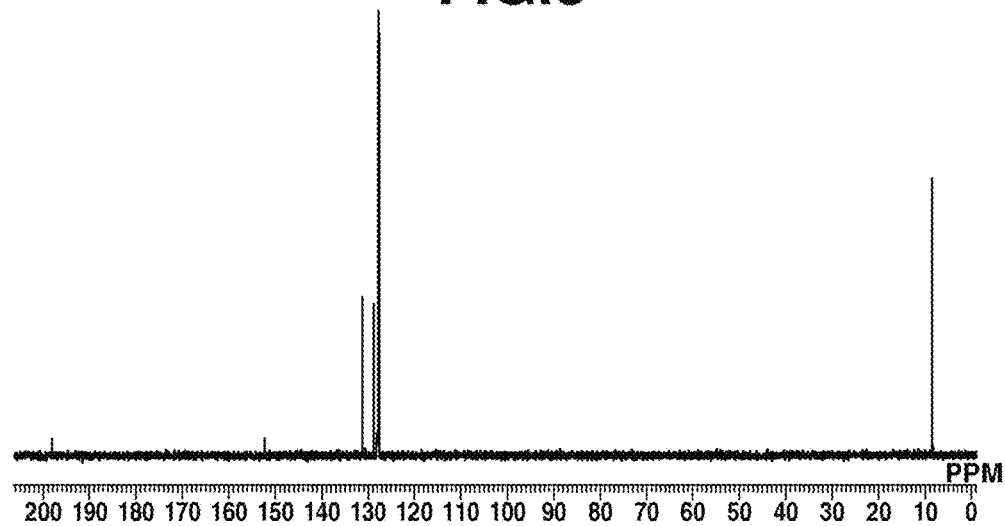
FIG. 3 is a diagram showing $^{13}$C-NMR spectrum of ruthenium complex A in Example 1.

A 100-mL Schlenk tube under argon atmosphere was charged with (η$^4$-1,3-cyclohexadiene)ruthenium(0) tricarbonyl complex (500 mg, 1.87 mmol) and 1,2-bis(dimethylsilyl)benzene (800 mg, 4.11 mmol), to which hexane (50 mL) which had been deaerated and dried was added. Under light irradiation using a high-pressure mercury lamp (UM-453B-A, 450 W, by Ushio Inc.), the contents were stirred at room temperature for 22 hours. After the completion of reaction, the reaction mixture was dried in vacuum. The dry product was dissolved in hexane (40 mL), from which a small amount of brown insoluble matter as by-product was removed by centrifugation. Thereafter, the hexane solution was concentrated under reduced pressure to about 25 mL. Subsequent recrystallization at −35° C. yielded ruthenium complex A (274 mg, 0.50 mmol, 27%) typically represented by formula (6). For the resulting ruthenium complex A, the geometry is shown in FIG. 1, the measurement results of $^1$H-NMR in FIG. 2, and the measurement results of $^{13}$C-NMR in FIG. 3.

$^1$H NMR (CDCl$_3$, 395 MHz): δ=−7.3 (s, Jsi-$_H$=16.8 Hz, 2H, Si—H), 0.75 (s, 24H, SiMe$_2$), 7.23-7.28 (m, 4H, C$_6$H$_4$), 7.53-7.58 (m, 4H, C$_6$H$_4$).

$^{13}$C NMR (CDCl$_3$, 395 MHz): δ=8.4, 128.9, 131.4, 152.5, 198.4.

IR (KBr pellet): ν=1975 (ν$_{Si-H}$), 1978 (ν$_{Ru-OH}$) cm$^{-1}$

Anal. calcd. for C$_{22}$H$_{34}$O$_2$RuSi$_4$:
C, 48.58; H, 6.30 Found: C, 48.34; H, 6.29.

Example 2

Synthesis of Ruthenium Complex B

Figure 4:
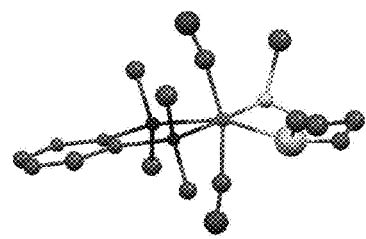
FIG. 4 illustrates the geometry of ruthenium complex B obtained in Example 2.
Figure 5:
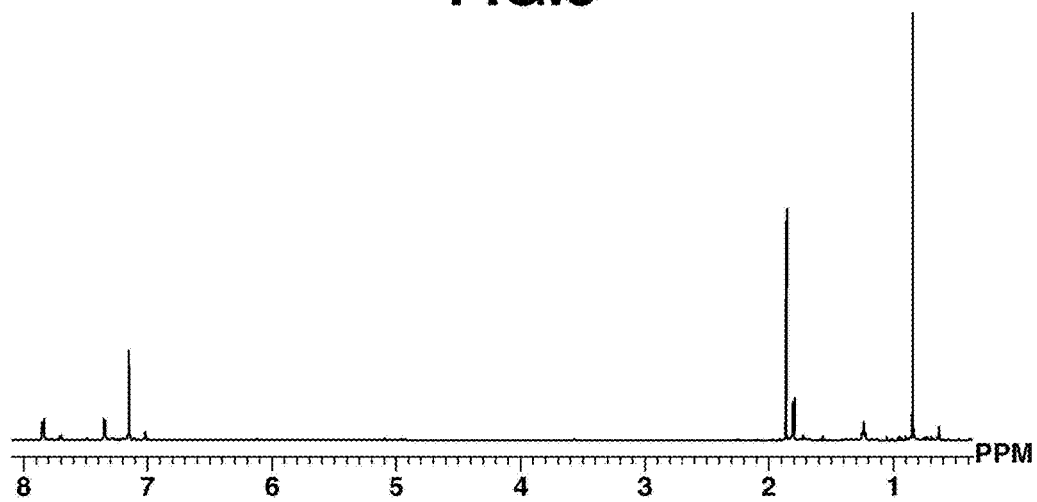
FIG. 5 is a diagram showing $^1$H-NMR spectrum of ruthenium complex B in Example 2.
Figure 6:
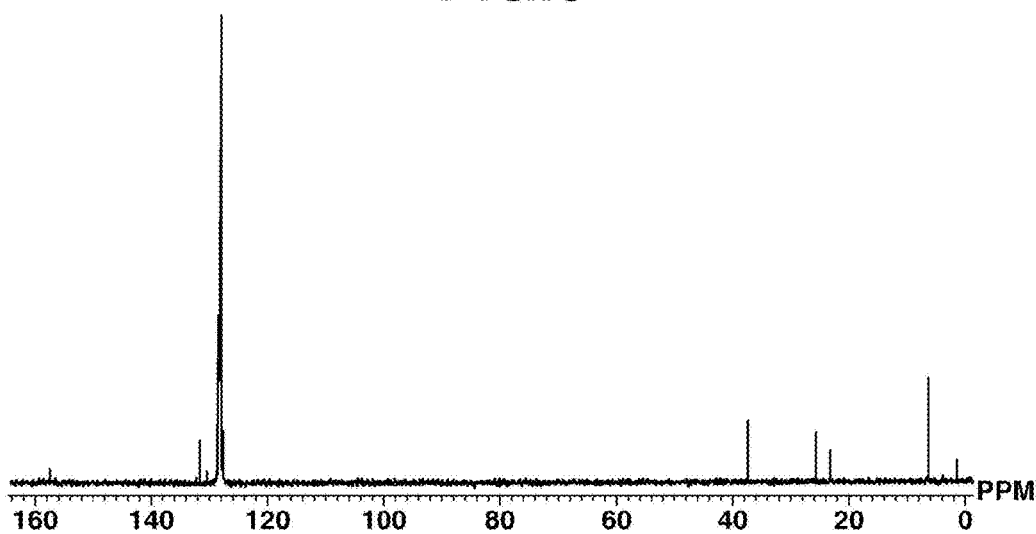
FIG. 6 is a diagram showing $^{13}$C-NMR spectrum of ruthenium complex B in Example 2.

In a 50-mL Schlenk tube under argon atmosphere, ruthenium complex A (100 mg, 0.18 mmol) was dissolved in toluene (20 mL) which had been deaerated and dried, to which 2,6-dithiaheptane (26 mg, 0.19 mmol) was added. The contents were stirred at room temperature for 12 hours. After the completion of reaction, the reaction mixture was dried in vacuum. The dry product was dissolved in diethyl ether (10 mL). Thereafter, the solution was concentrated under reduced pressure to about 5 mL. Subsequent recrystallization at −35° C. yielded ruthenium complex B (82 mg, 0.17 mmol, 94%) typically represented by formula (7). For the resulting ruthenium complex B, the geometry is shown in FIG. 4, the measurement results of $^1$H-NMR in FIG. 5, and the measurement results of $^{13}$C-NMR in FIG. 6.

$^1$H NMR (CDCl$_3$, 395 MHz): δ=0.82 (s, 12H, SiMe$_2$), 1.24 (quint, 2H, —CH$_2$CH$_2$CH$_2$—), 1.81 (t, 4H, —CH$_2$CH$_2$CH$_2$—), 1.87 (s, 6H, Sme), 7.32-7.38 (m, 2H, C$_6$H$_4$), 7.83-7.87 (m, 2H, C$_6$H$_4$).

$^{13}$C NMR (CDCl$_3$, 395 MHz): δ=1.53, 6.39, 23.1, 25.6, 37.4, 127.5, 131.6, 157.5.

Anal. Calcd. for C$_{22}$H$_{28}$O$_2$RuSi$_2$S$_2$:
C, 42.03; H, 5.81 Found: C, 42.21; H, 5.69.

(2) Hydrosilylation Reaction Using Ruthenium Complex a

Example 3

Hydrosilylation of 2-octene with 1,1,1,3,3-pentamethyldisiloxane

A 20-mL Schlenk tube equipped with a magnetic stirrer was heat dried while pumping to a vacuum of 5 Pa before its interior was purged with argon atmosphere. Into the Schlenk tube, ruthenium complex A (8 mg, 0.015 mmol) was admitted as catalyst. To the tube, 1-octene (78.2 μL, 0.5 mmol) was added, after which 1,1,1,3,3-pentamethyldisiloxane (97.6 μL, 0.5 mmol) was added. The solution was stirred at 80° C. for 3 hours. The solution was cooled, to which anisole (108.6 μL, 1.0 mmol, the amount used is identical hereinafter) was added as internal standard. By $^1$H-NMR spectroscopy, the geometry and yield of the product were determined. The results are shown as Entry 1 in Table 1.

$^1$H NMR (400 MHz, CDCl$_3$): δ=0.03 (s, 6H, Si(CH$_3$)$_2$), 0.06 (s, 9H, Si(CH$_3$)$_3$), 0.45-0.55 (m, 2H, SiCH$_2$), 0.88 (t, J$_{HH}$=7.2 Hz, 3H, CH$_2$CH$_3$), 1.20-1.34 (m, 12H, (CH$_2$)$_6$).

Example 4

Hydrosilylation of 2-octene with 1,1,1,3,5,5,5-heptamethyltrisiloxane

A 20-mL Schlenk tube equipped with a magnetic stirrer was heat dried while pumping to a vacuum of 5 Pa before its interior was purged with argon atmosphere. Into the Schlenk tube, ruthenium complex A (8 mg, 0.015 mmol) was admitted as catalyst. To the tube, 2-octene (78.2 μL, 0.5 mmol) was added, after which 1,1,1,3,5,5,5-heptamethyltrisiloxane (135.7 μL, 0.5 mmol) was added. The solution was stirred at 80° C. for 3 hours. The solution was cooled, to which anisole was added as internal standard. By $^1$H-NMR spectroscopy, the geometry and yield of the product were determined. The results are shown as Entry 2 in Table 1.

¹H NMR (600 MHz, CDCl₃): δ=−0.01 (s, 3H, SiC$\underline{H}$₃), 0.09 (s, 18H, (Si(C$\underline{H}$₃)₃)₂), 0.42-0.47 (m, 2H, SiC$\underline{H}$₂), 0.88 (t, $J_{HH}$=6.8 Hz, 3H, CH₂C$\underline{H}$₃), 1.23-1.33 (m, 12H, (C$\underline{H}$₂)₆).

Example 5

Hydrosilylation of 2-octene with Triethoxysilane

A 20-mL Schlenk tube equipped with a magnetic stirrer was heat dried while pumping to a vacuum of 5 Pa before its interior was purged with argon atmosphere. Into the Schlenk tube, ruthenium complex A (8 mg, 0.015 mmol) was admitted as catalyst. To the tube, 2-octene (78.2 µL, 0.5 mmol) was added, after which triethoxysilane (92.3 µL, 0.5 mmol) was added. The solution was stirred at 80° C. for 3 hours. The solution was cooled, to which anisole was added as internal standard substance. By ¹H-NMR spectroscopy, the geometry and yield of the product were determined. The results are shown as Entry 3 in Table 1.

¹H NMR (400 MHz, CDCl₃): δ=0.63 (m, 2H, Si(C$\underline{H}$₂)), 0.72 (t, 3H, C$\underline{H}$₃), 1.15 (t, $J_{HH}$=7.2 Hz, 9H, Si(OCH₂C$\underline{H}$₃)), 1.29 (m, 12H, C$\underline{H}$₂), 3.73 (q, $J_{HH}$=7.2 Hz, 9H, Si(OC$\underline{H}$₂CH₃)).

Example 6

Hydrosilylation of 2-octene with Triethylsilane

A 20-mL Schlenk tube equipped with a magnetic stirrer was heat dried while pumping to a vacuum of 5 Pa before its interior was purged with argon atmosphere. Into the Schlenk tube, ruthenium complex A (8 mg, 0.015 mmol) was admitted as catalyst. To the tube, 2-octene (78.2 µL, 0.5 mmol) was added, after which triethylsilane (79.8 µL, 0.5 mmol) was added. The solution was stirred at 80° C. for 3 hours. The solution was cooled, to which anisole was added as internal standard. By ¹H-NMR spectroscopy, the geometry and yield of the product were determined. The results are shown as Entry 4 in Table 1.

¹H NMR (400 MHz, CDCl₃): δ=0.51 (m, 8H, Si(C$\underline{H}$₂)₄), 0.84-1.04 (m, 12H, Si(CH₂C$\underline{H}$₃) and C$\underline{H}$₃), 1.18-1.38 (m, 12H, C$\underline{H}$₂).

TABLE 1

2-octene + Si—H $\xrightarrow[\text{80° C., 3 hrs}]{\text{Ru(Si)}_2\text{(Si—H)}_2\text{(CO)}_2 \text{ 3 mol \%}}$ hexyl~~~Si

| Entry | Si—H | Yield [a] |
|---|---|---|
| 1 | TMSOSiMe₂H | 16 |
| 2 | (TMSO)₂SiMeH | 15 |
| 3 | (EtO)₃SiH | 20 |
| 4 | Et₃SiH | 40 |

[a] Yield was determined by ¹H NMR analysis with anisole as an internal standard.

Example 7

Hydrosilylation of 1-octene with 1,1,1,3,3-pentamethyldisiloxane

A 20-mL Schlenk tube equipped with a magnetic stirrer was heat dried while pumping to a vacuum of 5 Pa before its interior was purged with argon atmosphere. Into the Schlenk tube, ruthenium complex A (8 mg, 0.015 mmol) was admitted as catalyst. To the tube, 1-octene (78.2 µL, 0.5 mmol) was added, after which 1,1,1,3,3-pentamethyldisiloxane (97.6 µL, 1.0 mmol) was added. The solution was stirred at 80° C. for 3 hours. The solution was cooled, to which anisole was added as internal standard. By ¹H-NMR spectroscopy, the geometry and yield of the product were determined. The results are shown as Entry 1 in Table 2.

¹H NMR (400 MHz, CDCl₃): δ=0.03 (s, 6H, Si(C$\underline{H}$₃)₂), 0.06 (s, 9H, Si(C$\underline{H}$₃)₃), 0.45-0.55 (m, 2H, SiC$\underline{H}$₂), 0.88 (t, $J_{HH}$=7.2 Hz, 3H, CH₂C$\underline{H}$₃), 1.20-1.34 (m, 12H, (C$\underline{H}$₂)₆).

Example 8

Hydrosilylation of 1-octene with 1,1,1,3,5,5,5-heptamethyltrisiloxane

A 20-mL Schlenk tube equipped with a magnetic stirrer was heat dried while pumping to a vacuum of 5 Pa before its interior was purged with argon atmosphere. Into the Schlenk tube, ruthenium complex A (8 mg, 0.015 mmol) was admitted as catalyst. To the tube, 1-octene (78.2 µL, 0.5 mmol) was added, after which 1,1,1,3,5,5,5-heptamethyltrisiloxane (135.7 µL, 0.5 mmol) was added. The solution was stirred at 80° C. for 3 hours. The solution was cooled, to which anisole was added as internal standard. By ¹H-NMR spectroscopy, the geometry and yield of the product were determined. The results are shown as Entry 2 in Table 2.

¹H NMR (600 MHz, CDCl₃): δ=−0.01 (s, 3H, SiC$\underline{H}$₃), 0.09 (s, 18H, (Si(C$\underline{H}$₃)₃)₂), 0.42-0.47 (m, 2H, SiC$\underline{H}$₂), 0.88 (t, $J_{HH}$=6.8 Hz, 3H, CH₂C$\underline{H}$₃), 1.23-1.33 (m, 12H, (C$\underline{H}$₂)₆).

Example 9

Hydrosilylation of cyclopentene with 1,1,1,3,3-pentamethyldisiloxane

A 20-mL Schlenk tube equipped with a magnetic stirrer was heat dried while pumping to a vacuum of 5 Pa before its interior was purged with argon atmosphere. Into the Schlenk tube, ruthenium complex A (8 mg, 0.015 mmol) was admitted as catalyst. To the tube, cyclopentene (44.2 µL, 0.5 mmol) was added, after which 1,1,1,3,3-pentamethyldisiloxane (97.6 µL, 0.5 mmol) was added. The solution was stirred at 80° C. for 3 hours. The solution was cooled, to which anisole was added as internal standard. By ¹H-NMR spectroscopy, the geometry and yield of the product were determined. The results are shown as Entry 3 in Table 2.

¹H NMR (400 MHz, C₆D₆): δ=0.10 (s, 6H, SiC$\underline{H}$₃), 0.13 (s, 9H, (Si(C$\underline{H}$₃)₃), 0.81-0.93 (m, 1H, SiC$\underline{H}$(CH₂)₂), 1.28-1.40 (m, 2H, CH₂), 1.46-1.63 (m, 4H, CH₂), 1.65-1.79 (m, 2H, CH₂).

TABLE 2

R~~R' + Si—H $\xrightarrow[\text{80° C., 3 hrs}]{\text{Ru(Si)}_2\text{(Si—H)}_2\text{(CO)}_2 \text{ 3 mol \%}}$ R''~~Si

| Entry | Olefin | Si—H | Yield [a] |
|---|---|---|---|
| 1 | 1-octene | TMSOSiMe₂H | 15 |
| 2 | 1-octene | (TMSO)₂SiMeH | 15 |
| 3 | cyclopentene | TMSOSiMe₂H | 17 |

[a] Yield was determined by ¹H NMR analysis with anisole as an internal standard.

(3) Hydrogenation Reaction Using Ruthenium Complex a

Example 10

Hydrogenation of Styrene

A 20-mL Schlenk tube equipped with a magnetic stirrer was heat dried while pumping to a vacuum of 5 Pa before its interior was purged with argon atmosphere. Into the Schlenk tube, ruthenium complex A (14 mg, 0.02 mmol) was admitted as catalyst and dissolved in toluene (1 mL). To the solution, styrene (57 µL, 0.5 mmol) was added. The solution was freeze deaerated, after which the Schlenk tube was purged with hydrogen atmosphere. The solution was stirred at room temperature for 3 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 1 in Table 3.

$^1$H NMR (CDCl$_3$, 395 MHz): δ=1.13 (t, $J_{HH}$=7.2 Hz, 3H, CH$_2$CH$_3$), 2.54 (q, $J_{HH}$=7.2 Hz, 2H, CH$_2$CH$_3$), 7.02-7.11 (m, 3H, C$_6$H$_5$), 7.11-7.20 (m, 2H, C$_6$H$_5$).

$^{13}$C NMR (100 MHz, CDCl$_3$): δ=15.6, 28.8, 125.6, 127.8, 128.3, 144.3.

Example 11

Hydrogenation of Trans-Stilbene

A 20-mL Schlenk tube equipped with a magnetic stirrer was heat dried while pumping to a vacuum of 5 Pa before its interior was purged with argon atmosphere. Into the Schlenk tube, ruthenium complex A (14 mg, 0.025 mmol) was admitted as catalyst and dissolved in toluene (1 mL). To the solution, trans-stilbene (90 mg, 0.5 mmol) was added. The solution was freeze deaerated, after which the Schlenk tube was purged with hydrogen atmosphere. The solution was stirred at room temperature for 6 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 2 in Table 3.

$^1$H NMR (CDCl$_3$, 395 MHz): δ=2.93 (s, 4H, CH$_2$), 7.12-7.23 (m, 6H, C$_6$H$_5$), 7.24-7.32 (m, 4H, C$_6$H$_5$).

$^{13}$C NMR (CDCl$_3$, 100 MHz): δ=37.9, 125.9, 128.3, 128.5, 141.8.

Example 12

Hydrogenation of Cyclohexene

A 20-mL Schlenk tube equipped with a magnetic stirrer was heat dried while pumping to a vacuum of 5 Pa before its interior was purged with argon atmosphere. Into the Schlenk tube, ruthenium complex A (14 mg, 0.025 mmol) was admitted as catalyst and dissolved in toluene (1 mL). To the solution, cyclohexene (54 µL, 0.5 mmol) was added. The solution was freeze deaerated, after which the Schlenk tube was purged with hydrogen atmosphere. The solution was stirred at room temperature for 6 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 3 in Table 3.

$^1$H NMR (CDCl$_3$, 395 MHz): δ=1.43 (s, 12H, CH$_2$).

$^{13}$C NMR (CDCl$_3$, 100 MHz): δ=27.0.

Example 13

Hydrogenation of Cyclopentene

A 20-mL Schlenk tube equipped with a magnetic stirrer was heat dried while pumping to a vacuum of 5 Pa before its interior was purged with argon atmosphere. Into the Schlenk tube, ruthenium complex A (14 mg, 0.025 mmol) was admitted as catalyst and dissolved in toluene (2 mL). To the solution, cyclopentene (44.2 µL, 0.5 mmol) was added. The solution was freeze deaerated, after which the Schlenk tube was purged with hydrogen atmosphere. The solution was stirred at room temperature for 6 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 4 in Table 3.

$^1$H NMR (CDCl$_3$, 395 MHz): δ=1.52 (s, 10H, CH$_2$).

$^{13}$C NMR (CDCl$_3$, 100 MHz): δ=25.9.

Example 14

Hydrogenation of 1-methyl-1-cyclohexene

A 20-mL Schlenk tube equipped with a magnetic stirrer was heat dried while pumping to a vacuum of 5 Pa before its interior was purged with argon atmosphere. Into the Schlenk tube, ruthenium complex A (14 mg, 0.025 mmol) was admitted as catalyst and dissolved in toluene (1 mL). To the solution, 1-methyl-1-cyclohexene (54 µL, 1.0 mmol) was added. The solution was freeze deaerated, after which the Schlenk tube was purged with hydrogen atmosphere. The solution was stirred at room temperature for 6 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 5 in Table 3.

$^1$H NMR (CDCl$_3$, 395 MHz) δ=0.86 (d, $J_{HH}$=5.8 Hz, 3H, CH$_3$), 1.04-1.28 (m, 4H, CH$_2$), 1.28-1.39 (m, 1H, CH), 1.54-1.72 (m, 6H, CH$_2$).

$^{13}$C NMR (CDCl$_3$, 100 MHz): δ=22.9, 26.3, 26.4, 32.7, 35.4.

Example 15

Hydrogenation of 2,3-dimethyl-2-butene

A 20-mL Schlenk tube equipped with a magnetic stirrer was heat dried while pumping to a vacuum of 5 Pa before its interior was purged with argon atmosphere. Into the Schlenk tube, ruthenium complex A (14 mg, 0.025 mmol) was admitted as catalyst and dissolved in toluene (1 mL). To the solution, 2,3-dimethyl-2-butene (54 µL, 1.0 mmol) was added. The solution was freeze deaerated, after which the Schlenk tube was purged with hydrogen atmosphere. The solution was stirred at room temperature for 6 hours. With anisole added as internal standard, the geometry and yield of the product were determined by $^1$H-NMR spectroscopy. The resulting compound was identified for geometry by $^1$H and $^{13}$C-NMR spectroscopy. The results are shown as Entry 6 in Table 3.

$^1$H NMR (CDCl$_3$, 395 MHz): δ=0.84 (d, $J_{HH}$=6.7 Hz, 12H, CH$_3$), 1.40 (septet, $J_{HH}$=6.7 Hz, 2H, CH).

$^{13}$C NMR (CDCl$_3$, 100 MHz): δ=19.4, 33.7.

TABLE 3

$$\text{olefin} \begin{pmatrix} R & R'' \\ R' & R''' \end{pmatrix} + H_2 \xrightarrow[\text{toluene, r.t., 6 hrs}]{\text{Ru(Si)}_2\text{(Si—H)}_2\text{(CO)}_2 \text{ 5 mol \%}} \begin{pmatrix} R & R'' \\ R' & R''' \end{pmatrix}$$

| Entry | Olefin | Yield |
|---|---|---|
| 1 [a] | styrene | 99 |
| 2 | trans-stilbene | 70 |
| 3 | cyclohexene | 96 |
| 4 | cyclopentene | 99 |
| 5 | (1-methylcyclohexene) | 33 |
| 6 | (2,3-dimethyl-2-butene) | 20 |

[a] Reaction time is 2 hours.

(4) Reductive Reaction of Amide Using Ruthenium Complex A

Example 16

Reduction of N,N-dimethyl-4-methoxybenzamide

A 20-mL eggplant flask equipped with a three-way cock and a magnetic stirrer was heat dried while pumping to a vacuum of 5 Pa before its interior was purged with argon atmosphere. Into the flask, ruthenium complex A (0.27 mg, $5.0 \times 10^{-4}$ mmol) was admitted as catalyst. To the flask, dimethylphenylsilane (681 µL) was added through a syringe, and N,N-dimethyl-4-methoxybenzamide (179 mg, 1.0 mmol) was added. The solution was stirred at 25° C. for 5 hours. The remaining dimethylphenylsilane was distilled off in vacuum. The crude product was purified by silica gel-packed column chromatography using hexane/ethyl acetate (10/1) as developing solvent, obtaining N,N-dimethyl-4-methoxybenzylamine (149 mg, 0.90 mmol, 90%). The results are shown as Entry 1 in Table 4. The resulting amine was identified for geometry by $^1$H and $^{13}$C-NMR spectroscopy and IR spectroscopy.

$^1$H NMR (CDCl$_3$, 395 MHz): δ=2.22 (s, 6H, NMe$_2$), 3.35 (s, 2H, CH$_2$), 3.80 (s, 3H, OMe), 6.85 (d, J=8.7 Hz, 2H, C$_6$H$_4$), 7.21 (d, J=8.7 Hz, 2H, C$_6$H$_4$).

$^{13}$C NMR (CDCl$_3$, 395 MHz): δ=45.22, 55.07, 63.74, 130.23, 113.58, 131.15, 158.71.

IR (neat): ν=1038, 1241, 1510, 2766, 2813, 2941 cm$^{-1}$.

Example 17

Reduction of N,N-dimethyl-4-bromobenzamide

A 20-mL eggplant flask equipped with a three-way cock and a magnetic stirrer was heat dried while pumping to a vacuum of 5 Pa before its interior was purged with argon atmosphere. Into the flask, ruthenium complex A (2.4 mg, $4.5 \times 10^{-3}$ mmol) was admitted as catalyst. To the flask, dimethylphenylsilane (681 µL) was added through a syringe, and N,N-dimethyl-4-bromobenzamide (228 mg, 1.0 mmol) was added. The solution was stirred at 25° C. for 23 hours. The remaining dimethylphenylsilane was distilled off in vacuum. The crude product was purified by silica gel-packed column chromatography using hexane/ethyl acetate (20/1) as developing solvent, obtaining N,N-dimethyl-4-bromobenzylamine (184 mg, 0.86 mmol, 86%). The results are shown as Entry 2 in Table 4. The resulting amine was identified for geometry by $^1$H and $^{13}$C-NMR spectroscopy and IR spectroscopy.

$^1$H NMR (CDCl$_3$, 395 MHz): δ=2.22 (s, 6H, NMe$_2$), 3.36 (s, 2H, CH$_2$), 7.18 (d, J=8.70 Hz, 2H, C$_6$H$_4$), 7.44 (d, J=8.70 Hz, 5H, C$_6$H$_4$).

$^{13}$C NMR (CDCl$_3$, 395 MHz): δ=45.97, 64.30, 121.45, 131.33, 131.97, 138.67.

IR (neat): ν=1011, 1487, 2767, 2815, 2941 cm$^{-1}$.

Example 18

Reduction of N,N-dimethyl-3-phenylpropanamide

A 20-mL eggplant flask equipped with a three-way cock and a magnetic stirrer was heat dried while pumping to a vacuum of 5 Pa before its interior was purged with argon atmosphere. Into the flask, ruthenium complex A (0.27 mg, $5.0 \times 10^{-4}$ mmol) was admitted as catalyst. To the flask, dimethylphenylsilane (681 µL) was added through a syringe, and N,N-dimethyl-3-phenylpropanamide (177 mg, 1.0 mmol) was added. The solution was stirred at 25° C. for 7 hours. The remaining dimethylphenylsilane was distilled off in vacuum. The crude product was purified by silica gel-packed column chromatography using hexane/ethyl acetate (10/1) as developing solvent, obtaining N,N-dimethyl-3-phenylpropylamine (151 mg, 0.79 mmol, 79%). The results are shown as Entry 3 in Table 4. The resulting amine was identified for geometry by $^1$H and $^{13}$C-NMR spectroscopy and IR spectroscopy.

$^1$H NMR (CDCl$_3$, 395 MHz): δ=1.80 (quint, J=7.7 Hz, 2H, CH$_2$), 2.23 (s, 6H, NMe$_2$), 2.30 (t, J=7.7 Hz, 2H, CH$_2$), 2.65 (t, J=7.7 Hz, 2H, CH$_2$), 7.24-7.16 (m, 3H, C$_6$H$_4$), 7.35-7.25 (m, 2H, C$_6$H$_4$).

$^{13}$C NMR (CDCl$_3$, 395 MHz): δ=29.57, 33.79, 45.60, 59.41, 125.84, 128.42, 128.50, 142.40.

IR (neat): ν=1030, 1496, 2764, 2942, 3025, 3060 cm$^{-1}$.

Example 19

Reduction of N-benzyl-ε-caprolactam

A 20-mL eggplant flask equipped with a three-way cock and a magnetic stirrer was heat dried while pumping to a vacuum of 5 Pa before its interior was purged with argon atmosphere. Into the flask, ruthenium complex A (0.27 mg, $5.0 \times 10^4$ mmol) was admitted as catalyst. To the flask, dimethylphenylsilane (681 µL) was added through a syringe, and N-benzyl-ε-caprolactam (203 mg, 1.0 mmol) was added. The solution was stirred at 25° C. for 7 hours. The remaining dimethylphenylsilane was distilled off in vacuum. The crude product was purified by silica gel-packed column chromatography using hexane/ethyl acetate (10/1) as developing solvent, obtaining 1-benzylazepane (165 mg, 0.87 mmol, 87%). The results are shown as Entry 4 in Table 4. The resulting amine was identified for geometry by $^1$H and $^{13}$C-NMR spectroscopy and IR spectroscopy.

$^1$H NMR (CDCl$_3$, 395 MHz): δ=1.58 (br, 8H, CH$_2$), 2.57 (d, J=5.8 Hz, 2H, CH$_2$), 3.60 (s, 2H, PhCH$_2$), 7.22-7.13 (m, 2H, C$_6$H$_4$), 7.33-7.22 (m, 3H, C$_6$H$_4$).

$^{13}$C NMR (CDCl$_3$, 395 MHz): δ=27.19, 28.40, 55.76, 62.90, 126.79, 128.22, 128.90, 140.30.

IR (neat): ν=1071, 1354, 1452, 2851, 2923 cm$^{-1}$.

TABLE 4

| Entry | Reactant | Catalyst concentration (mol %) | Reaction time (hr) | Reaction temperature (° C.) | Product | Yield (%) |
|---|---|---|---|---|---|---|
| 1 | 4-MeO-C6H4-C(O)-N(Me)2 | 0.05 | 5 | 25 | 4-MeO-C6H4-CH2-N(Me)2 | 90 |
| 2 | 4-Br-C6H4-C(O)-N(Me)2 | 0.45 | 23 | 25 | 4-Br-C6H4-CH2-N(Me)2 | 86 |
| 3 | Ph-CH2CH2-C(O)-N(Me)2 | 0.05 | 7 | 25 | Ph-CH2CH2-CH2-N(Me)2 | 79 |
| 4 | N-benzyl-ε-caprolactam | 0.05 | 7 | 25 | N-benzyl-azepane | 87 |

(5) Hydrosilylation Reaction Using Ruthenium Complex B

Example 20

Hydrosilylation of ethylene with 1,1,1,3,3-pentamethyldisiloxane

A 20-mL Schlenk tube equipped with a magnetic stirrer was heat dried while pumping to a vacuum of 5 Pa before its interior was purged with argon atmosphere. Into the Schlenk tube, ruthenium complex B (14 mg, 0.03 mmol) was admitted as catalyst. To the tube, 1,1,1,3,3-pentamethyldisiloxane (195.2 µL, 1.0 mmol) was added. The solution was freeze deaerated, after which the Schlenk tube was purged with ethylene atmosphere. The solution was stirred at 80° C. for 16 hours. After cooling, with anisole added as internal standard, the geometry and yield of the product were determined by $^1$H-NMR spectroscopy (yield 55%). The resulting compound was identified for geometry by $^1$H, $^{13}$C and $^{29}$Si-NMR spectroscopy.

$^1$H NMR (600 MHz, CDCl$_3$): δ=0.03 (s, 6H, Si(C$\underline{H}_3$)$_2$), 0.06 (s, 9H, Si(C$\underline{H}_3$)$_3$), 0.49 (q, J$_{HH}$=8.2 Hz, 2H, SiC$\underline{H}_2$CH$_3$), 0.92 (t, J$_{HH}$=8.2 Hz, 3H, CH$_2$C$\underline{H}_3$).

$^{13}$C NMR (100 MHz, CDCl$_3$): δ=−0.28, 1.93, 6.72, 10.03.

$^{29}$Si NMR (119 MHz, CDCl$_3$): δ=7.05, 8.60.

(6) Hydrogenation Reaction Using Ruthenium Complex B

Example 21

Hydrogenation of Styrene

A 20-mL Schlenk tube equipped with a magnetic stirrer was heat dried while pumping to a vacuum of 5 Pa before its interior was purged with argon atmosphere. Into the Schlenk tube, ruthenium complex B (12 mg, 0.025 mmol) was admitted as catalyst and dissolved in toluene (1 mL). To the solution, styrene (57 µL, 0.5 mmol) was added. The solution was freeze deaerated, after which the Schlenk tube was purged with hydrogen atmosphere. The solution was stirred at 100° C. for 16 hours. With anisole (108.6 µL, 1.0 mmol) added as internal standard, the geometry and yield of the product were determined by $^1$H-NMR spectroscopy (yield 71%). The resulting compound was identified for geometry by $^1$H and $^{13}$C-NMR spectroscopy.

$^1$H NMR (CDCl$_3$, 395 MHz): δ=1.13 (t, J$_{HH}$=7.2 Hz, 3H, CH$_2$C$\underline{H}_3$), 2.54 (q, J$_{HH}$=7.2 Hz, 2H, C$\underline{H}_2$CH$_3$), 7.02-7.11 (m, 3H, C$_6$H$_5$), 7.11-7.20 (m, 2H, C$_6$H$_5$).

$^{13}$C NMR (100 MHz, CDCl$_3$): δ=15.6, 28.8, 125.6, 127.8, 128.3, 144.3.

(7) Reductive Reaction of Amide Using Ruthenium Complex B

Example 22

Reduction of N,N-dimethyl-4-methoxybenzamide

A 20-mL eggplant flask equipped with a three-way cock and a magnetic stirrer was heat dried while pumping to a vacuum of 5 Pa before its interior was purged with argon atmosphere. Into the flask, ruthenium complex B (12 mg, 0.025 mmol) was admitted as catalyst and dissolved in toluene (0.25 mL). To the solution, 1,2-bis(dimethylsilyl)benzene (238 µL) was added through a syringe, and N,N-dimethyl-4-methoxybenzamide (90 mg, 0.5 mmol) was added. The solution was stirred at 100° C. for 16 hours. After cooling, with ferrocene (18.6 mg, 1.0 mmol) added as internal standard, the geometry and yield of the product were determined by $^1$H-NMR spectroscopy (yield 99%). The resulting compound was identified for geometry by $^1$H and $^{13}$C-NMR spectroscopy and IR spectroscopy.

$^1$H NMR (CDCl$_3$, 395 MHz): δ=2.22 (s, 6H, NMe$_2$), 3.35 (s, 2H, CH$_2$), 3.80 (s, 3H, OMe), 6.85 (d, J=8.7 Hz, 2H, C$_6$H$_4$), 7.21 (d, J=8.7 Hz, 2H, C$_6$H$_4$).

$^{13}$C NMR (CDCl$_3$, 395 MHz): δ=45.22, 55.07, 63.74, 130.23, 113.58, 131.15, 158.71.

IR (neat): ν=1038, 1241, 1510, 2766, 2813, 2941 cm$^{-1}$

The invention claimed is:

1. A mononuclear ruthenium complex having formula (1):

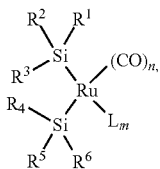

(1)

wherein:
m is 2;
n is 2; and
formula (1) is selected from the group consisting of:

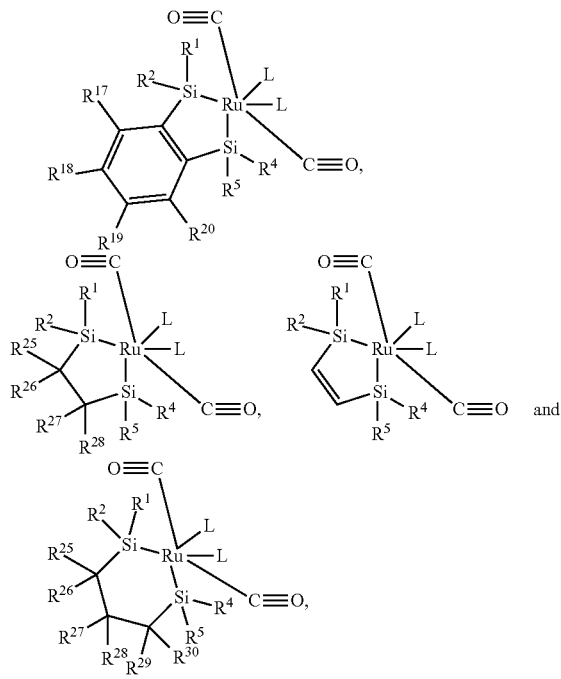

wherein:
each L is independently molecular hydrogen, N(R)$_3$, RC(=NR)R, pyrrolyl, imidazolyl, pyridinyl, pyrimidinyl, oxazolinyl, isoxazolinyl, As(R)$_3$, ROH, RSH, ROR, RSR, RC≡N, RN≡C, RC(O)H, RC(O)R, C$_2$-C$_{30}$ alkenyl, C$_2$-C$_{30}$ alkynyl or R$^1$R$^2$R$^3$SiH;
each R is independently C$_1$-C$_{30}$ alkyl, C$_6$-C$_{30}$ aryl or C$_7$-C$_{30}$ aralkyl;
R$^1$, R$^2$, R$^3$, R$^4$ and R$^5$ are each independently hydrogen or alkyl, aryl, aralkyl, organooxy, monoorganoamino, diorganoamino, monoorganophosphino, diorganophosphino, monoorganosilyl, diorganosilyl, triorganosilyl or organothio, each of which is independently and optionally substituted with X;
R$^{17}$, R$^{18}$, R$^{19}$ and R$^{20}$ are each independently hydrogen, halogen, C$_1$-C$_{10}$ alkyl or C$_1$-C$_{10}$ alkoxy;
R$^{25}$, R$^{26}$, R$^{27}$, R$^{28}$, R$^{29}$ and R$^{30}$ are each independently hydrogen, C$_1$-C$_{20}$ alkyl, C$_1$-C$_{20}$ aralkyl or C$_6$-C$_{20}$ aryl; and X is halogen, organooxy, monoorganoamino, diorganoamino or organothio;
with the proviso that two L may bond together.

2. The mononuclear ruthenium complex of claim 1, wherein:
each L is independently RSH, RSR or R$^1$R$^2$R$^3$SiH.

3. The mononuclear ruthenium complex of claim 2, wherein:
each L is independently R$^1$R$^2$R$^3$SiH, wherein R$^1$R$^2$R$^3$SiH in one L is represented by R$^7$R$^8$R$^9$SiH and R$^1$R$^2$R$^3$SiH in the other L is represented by R$^{10}$R$^{11}$R$^{12}$SiH;
R$^7$, R$^8$ and R$^9$ are each independently alkyl, aryl or aralkyl;
R$^{10}$, R$^{11}$ and R$^{12}$ are each independently alkyl, aryl or aralkyl; and
(i) one pair of R$^7$, R$^8$ and R$^9$, taken together, form a crosslinking substituent selected from the group consisting of —O—, —S—, —NH—, —NR—, —PR—, —NH—(CH$_2$)$_k$—NH—, —NR—(CH$_2$)$_k$—NR—, —PH—(CH$_2$)$_k$—PH—, —PR—(CH$_2$)$_k$—PR—, —CH=CH—, —CR=CR—, C$_1$-C$_{10}$ alkylene, C$_6$-C$_{30}$ arylene, C$_7$-C$_{30}$ aralkylene, —(CH$_2$O)$_k$—, (CH$_2$O)$_k$—O—(CH$_2$)$_k$—, —O—(CH$_2$O)$_k$—O—, —R'—O—(CH$_2$O)$_k$—O—R'—, —(CH$_2$S)$_k$—, (CH$_2$)$_k$—S—(CH$_2$)$_k$—, —S—(CH$_2$)$_k$—S—, —R'—S—(CH$_2$)$_k$—O—R'—, —Si(R)$_2$— and —(CH$_2$)$_k$—Si(R)$_2$—(CH$_2$)$_k$—; or
(ii) one pair of R$^{10}$, R$^{11}$ and R$^{12}$, taken together, form a crosslinking substituent selected from the group consisting of —O—, —S—, —NH—, —NR—, —PR—, —NH—(CH$_2$)$_k$—NH—, —NR—(CH$_2$)$_k$—NR—, —PH—(CH$_2$)$_k$—PH—, —PR—(CH$_2$)$_k$—PR—, —CH=CH—, —CR=CR—, C$_1$-C$_{10}$ alkylene, C$_6$-C$_{30}$ arylene, C$_7$-C$_{30}$ aralkylene, —(CH$_2$O)$_k$—, (CH$_2$O)$_k$—O—(CH$_2$)$_k$—, —O—(CH$_2$O)$_k$—O—, —R'—O—(CH$_2$O)$_k$—O—R'—, —(CH$_2$S)$_k$—, (CH$_2$)$_k$—S—(CH$_2$)$_k$—, —S—(CH$_2$)$_k$—S—, —R'—S(CH$_2$)$_k$—O—R'—, —Si(R)$_2$— and —(CH$_2$)$_k$—Si(R)$_2$—(CH$_2$)$_k$—;
each R is independently C$_1$-C$_{30}$ alkyl, C$_6$-C$_{30}$ aryl or C$_7$-C$_{30}$ aralkyl;
each R' is independently C$_1$-C$_{10}$ alkylene; and
each k is independently 1, 2, 3, 4, 5, 6, 7 8, 9, or 10.

4. The mononuclear ruthenium complex of claim 3, wherein:
one pair of R$^7$, R$^8$ and R$^9$, taken together, form a crosslinking substituent.

5. The mononuclear ruthenium complex of claim 4, wherein:
formula (1) is represented by:

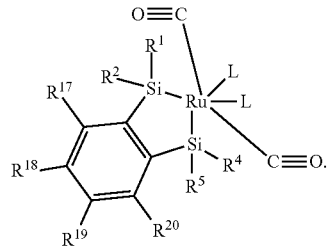

6. The mononuclear ruthenium complex of claim 2, wherein:
(a) (i) one L is RSH, wherein RSH is represented by R$^{13}$SH or R$^{14}$SH, and the other L is RSR, wherein RSR is represented by $R^{15}SR^{16}$, or (ii) one L is RSR, wherein RSR is represented by $R^{13}SR^{14}$, and the other L is RSH, wherein RSH is represented by $R^{15}SH$ or $R^{16}SH$;

$R^{13}$ and $R^{14}$ are each independently $C_1$-$C_{30}$ alkyl, $C_6$-$C_{30}$ aryl or $C_7$-$C_{30}$ aralkyl;

$R^{15}$ and $R^{16}$ are each independently $C_1$-$C_{30}$ alkyl, $C_6$-$C_{30}$ aryl or $C_7$-$C_{30}$ aralkyl; and at least one pair of any one of $R^{13}$ and $R^{14}$ and any one of $R^{15}$ and $R^{16}$, taken together, form a crosslinking substituent selected from the group consisting of —O—, —S—, —NH—, —NR—, —PR—, —NH—$(CH_2)_k$—NH—, —NR—$(CH_2)_k$—NR—, —PH—$(CH_2)_k$—PH—, —PR—$(CH_2)_k$—PR—, —CH=CH—, —CR=CR—, $C_1$-$C_{10}$ alkylene, $C_6$-$C_{30}$ arylene, $C_7$-$C_{30}$ aralkylene, —$(CH_2O)_k$—, $(CH_2O)_k$—O—$(CH_2)_k$—, —O—$(CH_2O)_k$—O—, —R'—O—$(CH_2O)_k$—O—R'—, —$(CH_2S)_k$—, $(CH_2)_k$—S—$(CH_2)_k$—, —S—$(CH_2)_k$—S—, —R'—S—$(CH_2)_k$—O—R'—, —Si(R)$_2$— and —$(CH_2)_k$—Si(R)$_2$—$(CH_2)_k$—;

each R is independently $C_1$-$C_{30}$ alkyl, $C_6$-$C_{30}$ aryl or $C_7$-$C_{30}$ aralkyl;

each R' is independently $C_1$-$C_{10}$ alkylene; and each k is independently 1, 2, 3, 4, 5, 6, 7 8, 9, or 10; or (b) one L is RSH, wherein RSH is represented by $R^{13}SH$ or $R^{14}SH$, and the other L is RSH, wherein RSH is represented by $R^{15}SH$ or $R^{16}SH$;

$R^{13}$ and $R^{14}$ are each independently $C_1$-$C_{30}$ alkyl, $C_6$-$C_{30}$ aryl or $C_7$-$C_{30}$ aralkyl;

$R^{15}$ and $R^{16}$ are each independently $C_1$-$C_{30}$ alkyl, $C_6$-$C_{30}$ aryl or $C_7$-$C_{30}$ aralkyl; and at least one pair of any one of $R^{13}$ and $R^{14}$ and any one of $R^{15}$ and $R^{16}$, taken together, form a crosslinking substituent selected from the group consisting of —O—, —S—, —NH—, —NR—, —PR—, —NH—$(CH_2)_k$—NH—, —NR—$(CH_2)_k$—NR—, —PH—$(CH_2)_k$—PH—, —PR—$(CH_2)_k$—PR—, —CH=CH—, —CR=CR—, $C_1$-$C_{10}$ alkylene, $C_6$-$C_{30}$ arylene, $C_7$-$C_{30}$ aralkylene, —$(CH_2O)_k$—, $(CH_2O)_k$—O—$(CH_2)_k$—, —O—$(CH_2O)_k$—O—, —R'—O—$(CH_2O)_k$—O—R'—, —$(CH_2S)_k$—, $(CH_2)_k$—S—$(CH_2)_k$—, —S—$(CH_2)_k$—S—, —R'—S—$(CH_2)_k$—O—R'—, —Si(R)$_2$— and —$(CH_2)_k$—Si(R)$_2$—$(CH_2)_k$—;

each R is independently $C_1$-$C_{30}$ alkyl, $C_6$-$C_{30}$ aryl or $C_7$-$C_{30}$ aralkyl;

each R' is independently $C_1$-$C_{10}$ alkylene; and each k is independently 1, 2, 3, 4, 5, 6, 7 8, 9, or 10; or (c) one L is RSR, wherein RSR is represented by $R^{13}SR^{14}$, and the other L is RSR, wherein RSR is represented by $R^{15}SR^{16}$;

$R^{13}$ and $R^{14}$ are each independently $C_1$-$C_{30}$ alkyl, $C_6$-$C_{30}$ aryl or $C_7$-$C_{30}$ aralkyl;

$R^{15}$ and $R^{16}$ are each independently $C_1$-$C_{30}$ alkyl, $C_6$-$C_{30}$ aryl or $C_7$-$C_{30}$ aralkyl; and at least one pair of any one of $R^{13}$ and $R^{14}$ and any one of $R^{15}$ and $R^{16}$, taken together, form a crosslinking substituent selected from the group consisting of —O—, —S—, —NH—, —NR—, —PR—, —NH—$(CH_2)_k$—NH—, —NR—$(CH_2)_k$—NR—, —PH—$(CH_2)_k$—PH—, —PR—$(CH_2)_k$—PR—, —CH=CH—, —CR=CR—, $C_1$-$C_{10}$ alkylene, $C_6$-$C_{30}$ arylene, $C_7$-$C_{30}$ aralkylene, —$(CH_2O)_k$—, $(CH_2O)_k$—O—$(CH_2)_k$—, —O—$(CH_2O)_k$—O—, —R'—O—$(CH_2O)_k$—O—R'—, —$(CH_2S)_k$—, $(CH_2)_k$—S—$(CH_2)_k$—, —S—$(CH_2)_k$—S—, —R'—S—$(CH_2)_k$—O—R'—, —Si(R)$_2$— and —$(CH_2)_k$—Si(R)$_2$—$(CH_2)_k$—;

each R is independently $C_1$-$C_{30}$ alkyl, $C_6$-$C_{30}$ aryl or $C_7$-$C_{30}$ aralkyl;

each R' is independently $C_1$-$C_{10}$ alkylene; and each k is independently 1, 2, 3, 4, 5, 6, 7 8, 9, or 10.

7. The mononuclear ruthenium complex of claim 6, wherein:

(a) (i) one L is RSH, wherein RSH is represented by $R^{13}SH$ or $R^{14}SH$, and the other L is RSR, wherein RSR is represented by $R^{15}SR^{16}$, or (ii) one L is RSR, wherein RSR is represented by $R^{13}SR^{14}$, and the other L is RSH, wherein RSH is represented by $R^{15}SH$ or $R^{16}SH$; and at least one pair of any one of $R^{13}$ and $R^{14}$ and any one of $R^{15}$ and $R^{16}$, taken together, form a crosslinking substituent; or (b) one L is RSH, wherein RSH is represented by $R^{13}SH$ or $R^{14}SH$, and the other L is RSH, wherein RSH is represented by $R^{15}SH$ or $R^{16}SH$; and at least one pair of any one of $R^{13}$ and $R^{14}$ and any one of $R^{15}$ and $R^{16}$, taken together, form a crosslinking substituent.

8. The mononuclear ruthenium complex of claim 6, wherein:

formula (1) is represented by:

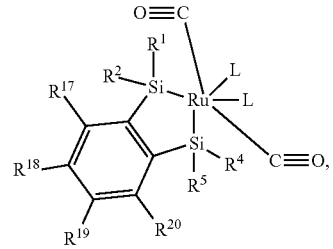

wherein:

at least one pair of any one of $R^{13}$ and $R^{14}$ and any one of $R^{15}$ and $R^{16}$, taken together, form a $C_1$-$C_6$ alkylene.

9. A method for preparing an alkylsilane or cycloalkylsilane, comprising the step of reacting an alkene or cycloalkene with a hydrosilane or organohydropolysiloxane having a Si—H bond in the presence of the mononuclear ruthenium complex of claim 1.

10. A method for preparing an alkane or cycloalkane comprising the step of hydrogenating an alkene or cycloalkene in the presence of the mononuclear ruthenium complex of claim 1.

11. A method for preparing a linear, branched, or cyclic amine, comprising the step of reducing (i) a linear or branched amide or (ii) a lactam with a silane or organohydropolysiloxane having a Si—H bond in the presence of the mononuclear ruthenium complex of claim 1.

\* \* \* \* \*